United States Patent
Yokosawa et al.

(10) Patent No.: US 8,693,760 B2
(45) Date of Patent: Apr. 8, 2014

(54) MEDICAL IMAGING APPARATUS

(75) Inventors: Suguru Yokosawa, Kokubunji (JP); Yo Taniguchi, Kokubunji (JP); Yoshitaka Bito, Kokubunji (JP)

(73) Assignee: Hitachi Medical Corporation, Tokyo (JP)

( * ) Notice: Subject to any disclaimer, the term of this patent is extended or adjusted under 35 U.S.C. 154(b) by 146 days.

(21) Appl. No.: 13/380,201

(22) PCT Filed: Jun. 22, 2010

(86) PCT No.: PCT/JP2010/060557
§ 371 (c)(1),
(2), (4) Date: Dec. 22, 2011

(87) PCT Pub. No.: WO2010/150783
PCT Pub. Date: Dec. 29, 2010

(65) Prior Publication Data
US 2012/0093385 A1      Apr. 19, 2012

(30) Foreign Application Priority Data
Jun. 25, 2009   (JP) .................................. 2009-151338

(51) Int. Cl.
*G06K 9/00*      (2006.01)

(52) U.S. Cl.
USPC .......................................................... 382/131

(58) Field of Classification Search
None
See application file for complete search history.

(56) References Cited

U.S. PATENT DOCUMENTS

| | | | |
|---|---|---|---|
| 5,514,957 A * | 5/1996 | Tatebayashi .................. | 324/309 |
| 5,545,993 A * | 8/1996 | Taguchi et al. ............... | 324/309 |
| 2008/0009709 A1 * | 1/2008 | Guehring et al. ............. | 600/414 |

* cited by examiner

*Primary Examiner* — Nirav G Patel
(74) *Attorney, Agent, or Firm* — Antonelli, Terry, Stout & Kraus, LLP.

(57) ABSTRACT

There is provided a technique for, in a medical imaging apparatus enabling imaging of an arbitrary plane in a three-dimensional space, enabling automatic calculation of a slice position and automatic calculation of an extracting slice in MPR, without prolonging examination time. Two-dimensional scout scan similar to that used for manual setting of a slice position is performed, and the obtained scout images are processed to calculate a recommended slice position. Algorithms for the processing and various image processing procedures used for the processing are stored beforehand for every type of imaging region and every type of examination.

15 Claims, 15 Drawing Sheets

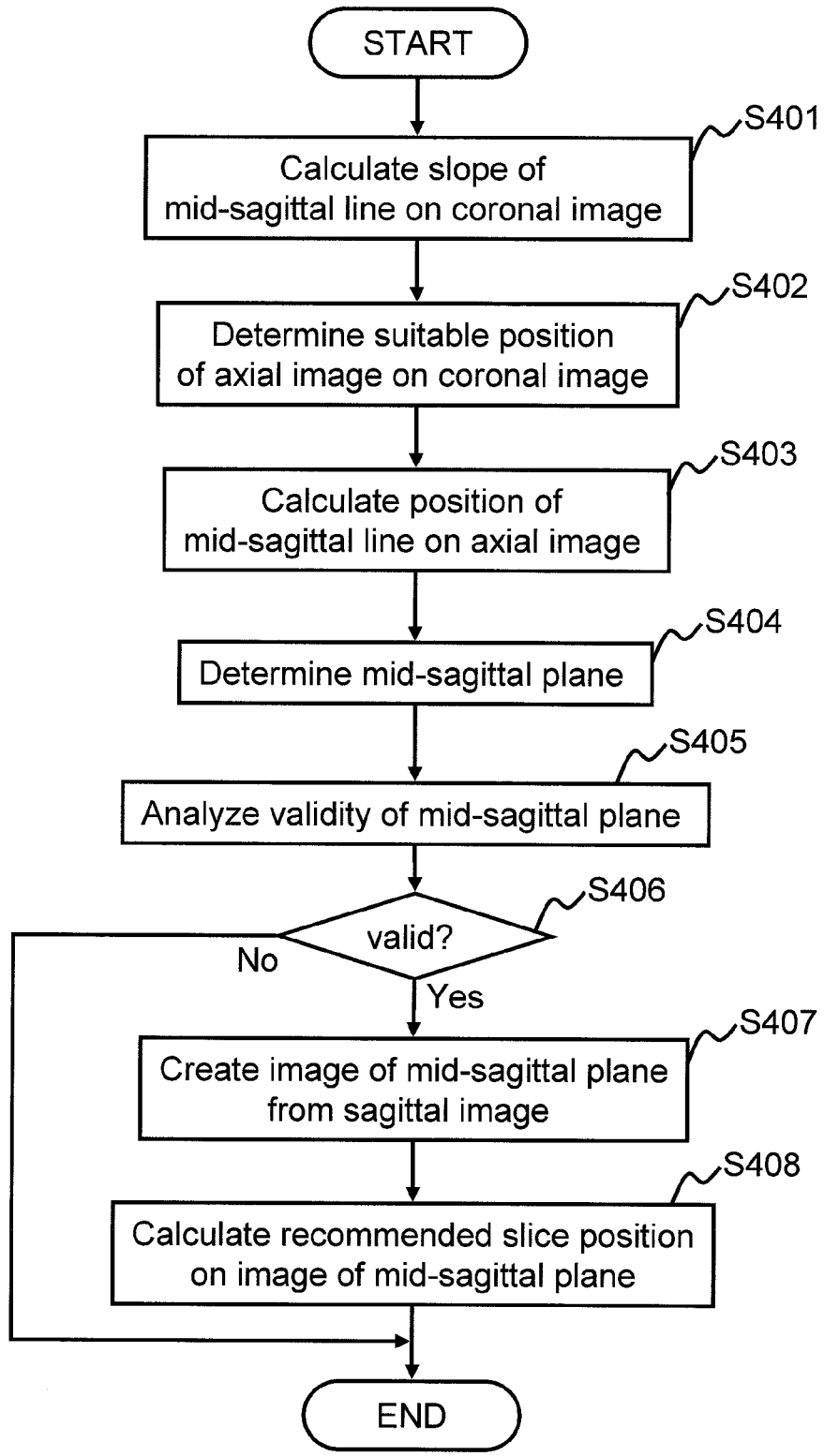

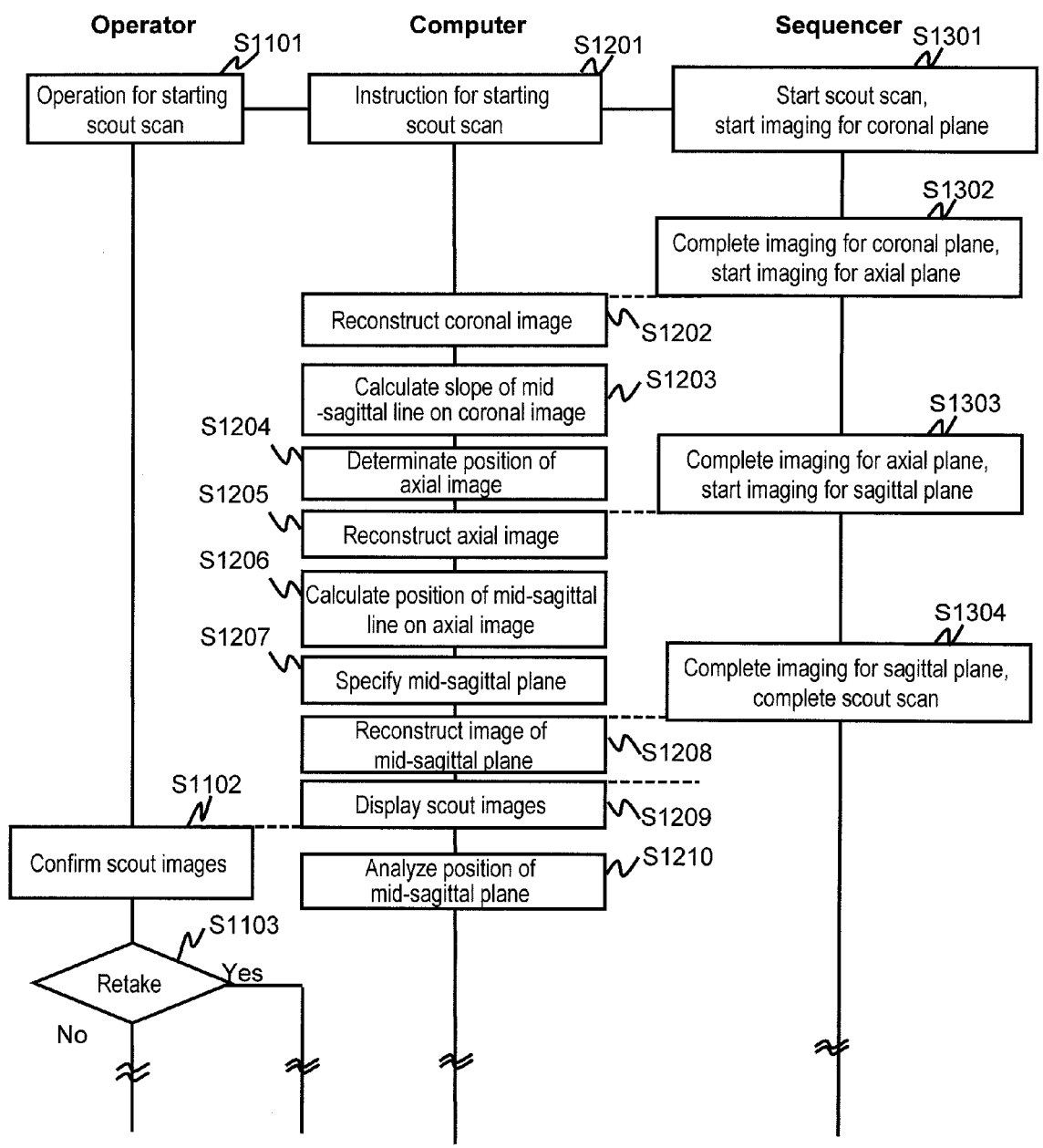

MEDICAL IMAGING APPARATUS

TECHNICAL FIELD

The present invention relates to a technique for determining a position of a slice position and a technique for extracting a diagnostic image for use in an examination using a medical imaging apparatus such as a magnetic resonance imaging apparatus.

BACKGROUND ART

There are medical imaging apparatuses enabling imaging of a slice of desired position and orientation in a three-dimensional space for use of the obtained image in diagnosis. In particular, magnetic resonance imaging (MRI) apparatuses are medical diagnostic imaging apparatuses utilizing the nuclear magnetic resonance phenomenon of, mainly, proton, which apparatuses apply a radio frequency magnetic field to a subject placed in a static magnetic field to excite nuclear magnetization, and construct images from measured magnetic resonance signals. The MRI apparatuses enable noninvasive imaging of an arbitrary slice without any restriction concerning imaging region.

In the MRI apparatuses, in general, a slice gradient magnetic field for determining a slice to be imaged (slice position scan plane) and an excitation pulse for exciting magnetization in the scan plane are applied at the same time to obtain nuclear magnetic resonance signals generated by the excited magnetization. In order to add positional information to the magnetization, during the period from the excitation to the acquirement of the echo signals, a phase encoding gradient magnetic field and a read-out gradient magnetic field are applied to the magnetization in the scan plane.

In the medical diagnostic imaging apparatuses enable to image an arbitrary slice, such as MRI apparatuses, a slice position should be set beforehand. For this reason, in an examination, scout scan for setting a slice position is performed before the main scan for obtaining an image for diagnosis.

Since the slice position is generally determined according to an examination region or target disease, the slice position is manually set by an operator through a user interface using a scout image. The examination may be performed as a combination of imaging of different slice positions, or periodically repeated imaging of the same slice position. When imaging different slice positions, an operator is required to set the slice position for every imaging. Further, when imaging the same slice position repeatedly, it is difficult for the operator to set the same slice position for every imaging by a manual operation. In any case, the same operation for setting the slice position must be repeated for every imaging, and it is mentioned as one of monotonous troublesome operations.

In order to improve the operability of such operation for determining a slice position, there are proposed, for example, a positioning operation made easier by visual effect (refer to, for example, Patent document 1), an automatic positioning based on image recognition (refer to, for example, Non-patent documents 1 and 2), and so forth. As the effect of the automatization, not only the improvement in the operability, but also improvement in reproducibility of the slice position at the time of the follow-up examination is expected.

PRIOR ART REFERENCES

Patent Document

Patent document 1: Japanese Patent Unexamined Publication (KOKAI) No. 05-269113

Non-Patent Documents

Non-patent document 1: Young S., Bystrov D., Netsch T., Bergmans R., van Muiswinkel A., Visser F., Springorum R., and Gieseke J., "Automated planning of MRI neuro scans", In Medical Imaging: Image Processing, Reinhardt J. M., ed., Proc. of SPIE, Vol. 6144, 2006 Non-patent document 2: Itti L., Chang L., and Ernst T., "Automated Scan Prescription for Brain MRI", In Magnetic Resonance in Medicine, 45:486-494, 2001

SUMMARY OF THE INVENTION

Problem to be Solved by the Invention

Since the technique disclosed in Patent document 1 still includes a step based on a manual operation carried out by an operator, it still suffers from poor reproducibility and troublesomeness. Further, in the techniques disclosed in Non-patent documents 1 and 2, it is necessary to measure three-dimensional volume data as a scout image, the time required for the scout scan is longer than that conventionally required. Furthermore, since the slice position is calculated and determined after the scout scan, processing time for automatization is further required. For these reasons, not only they suffer from a prolonged whole examination time, but also they give stress to an operator due to the waiting time required for processing for automatization. Thus, they do not fully meet the demand of operators.

In recent years, with improvement in high-speed imaging techniques such as parallel imaging, three-dimensional imaging for obtaining a three-dimensional image at high speed is carried out. Since a three-dimensional space may be set as an imaging area in the three-dimensional imaging, it is easier than the two-dimensional imaging, in which a slice is set. However, after completion of imaging, it is necessary to extract a two-dimensional image desired for diagnosis from the obtained three-dimensional volume data. This processing is called multi planar reconstruction (MPR), and an image processing system enabling easy and high speed extraction of a two-dimensional image is desired.

The present invention was accomplished with taking the above problems into consideration, and an object thereof is to provide, for use in a medical imaging apparatus in which an arbitrary slice in a three-dimensional space can be set as a slice position, such as the aforementioned MRI apparatuses, a technique enabling automatic calculation of a slice position and automatic calculation of an extracting slice in MPR without changing the conventional examination flow and without prolonging the examination time.

Means to Solve the Problem

According to the present invention, two-dimensional scout scan is performed in the same manner as in the case where a slice position is manually set, and the obtained scout image is processed to calculate a recommended slice position. Algorithms and various image processing procedures used for the processing are stored beforehand for every kind of imaging region and examination.

Specifically, there is provided a medical imaging apparatus enabling imaging of an arbitrary slice in a three-dimensional space, which comprises an image acquiring means for acquiring a first image group consisting of one or more two-dimensional images parallel to a first slice plane, which is one of mutually crossing two slice planes, and a second image group consisting of one or more two-dimensional images parallel to a second slice plane, which is the other of the mutually crossing two slice planes, an extracting means of anatomical feature for extracting information on an anatomical feature defined beforehand from a two-dimensional image, a calculating means of recommended slice position for calculating a recommended slice position to be recommended as a slice position, and an information storing means of recommended slice position calculation for storing recommended slice position calculation information necessary for calculating the recommended slice position according to an imaging region, wherein the extracting means of anatomical feature extracts information on a first anatomical feature from the first image group, and extracts information on a second anatomical feature from the second image group, and the calculating means of recommended slice position calculates the recommended slice position by using the information on the first anatomical feature and the information on the second anatomical feature according to the recommended slice position calculation information.

Effect of the Invention

According to the present invention, in a medical imaging apparatus in which an arbitrary slice in a three-dimensional space can be set as a slice position, such as the aforementioned MRI apparatuses, a slice position can be automatically calculated, and an extracting slice can be automatically calculated in MPR without changing the conventional examination flow and without prolonging the examination time.

BRIEF DESCRIPTION OF THE DRAWINGS

FIG. 4 is a flowchart of recommended slice position calculation processing according to the first embodiment.

FIG. 11 is a chart for explaining measurement preparation processing according to the first embodiment.

MODES FOR CARRYING OUT THE INVENTION

First Embodiment

Hereafter, the first embodiment of the present invention will be explained. In all of the drawings for explaining the embodiments of the present invention, elements having the same function are indicated with the same numerals or symbols, and repetitive explanations thereof are omitted.

Figure 1:
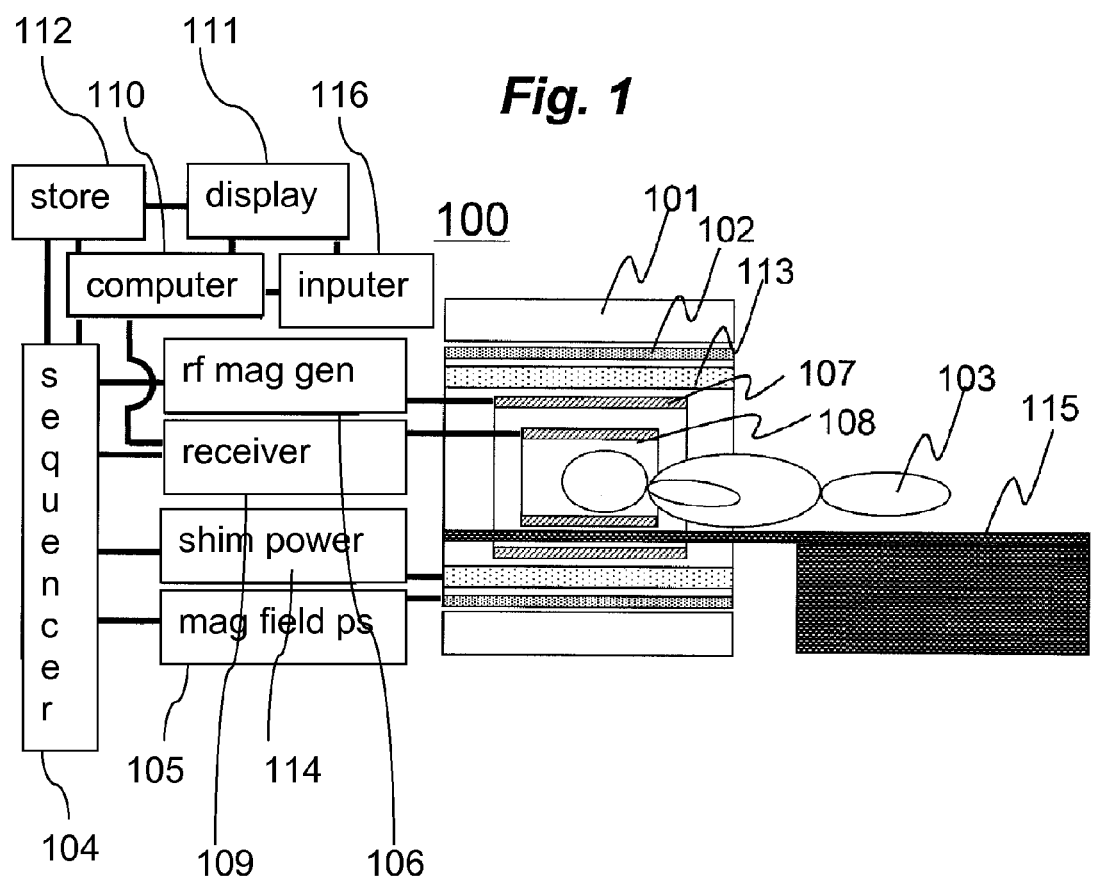
FIG. 1 is a block diagram showing a typical configuration of an MRI apparatus according to the first embodiment.

First, a magnetic resonance imaging (MRI) apparatus of this embodiment will be explained. An MRI apparatus 100 of this embodiment applies a radio frequency magnetic field to a subject 103 placed in a static magnetic field to excite nuclear magnetization in the subject 103, and measures generated magnetic resonance signals (echo signals), as described above. In this operation, a gradient magnetic field is applied to add positional information to the magnetic resonance signals to be measured for obtaining an image (imaging). FIG. 1 is a block diagram showing a typical configuration of the MRI apparatus 100 according to this embodiment, which implements the above operation. The MRI apparatus 100 of this embodiment is provided with a magnet 101 for generating a static magnetic field, a gradient magnetic field coil 102 for generating a gradient magnetic field, an RF coil 107 for irradiating a radio frequency magnetic field pulse (henceforth referred to as RF pulse) on the subject (living body) 103, an RF probe 108 for detecting the echo signals generated by the subject 103, and a bed (table) 115 for placing the subject (for example, living body) 103 thereon in the space of the static magnetic field generated by the magnet 101.

The MRI apparatus 100 according to this embodiment further is provided with a gradient magnetic field power supply 105 for driving the gradient magnetic field coil 102, a radio frequency magnetic field generator 106 for driving the RF coil 107, a receiver 109 for receiving the echo signals detected by the RF probe 108, a sequencer 104 for sending commands to the gradient magnetic field power supply 105 and the radio frequency magnetic field generator 106 to generate a gradient magnetic field and a radio frequency magnetic field, and setting a nuclear magnetic resonance frequency used as the basis of detection in the receiver 109, a computer 110 for executing signal processing using the detected signals, a display 111 for displaying the results of the processing executed by the computer 110, a storage device 112 for storing the processing results, and an input device 116 for receiving directions from an operator.

In the MRI apparatus 100 having the above configuration, under the control by the sequencer 104, an RF pulse is applied to the subject 103 through the RF coil 107, and a gradient magnetic field pulse for adding positional information, such as that for slice selection and phase encoding, to the echo signals is applied by the gradient magnetic field coil 102. Further, signals generated from the subject 103 are received by the RF probe 108, and the detected signals are sent to the computer 110, and subjected to a signal processing such as image reconstruction therein. The storage device 112 may store not only the results of signal processing, but also the detected signals themselves, imaging conditions etc., if needed.

The MRI apparatus 100 may further be provided with a shim coil 113, and a shim power supply 114 for driving the shim coil 113, when it is necessary to control uniformity of the static magnetic field. The shim coil 113 is provided with a plurality of channels, and generates additional magnetic fields for correcting non-uniformity of the static magnetic field with an electric current supplied from the shim power supply 114. The electric currents flown into the channels constituting the shim coil 113 at the time of adjusting uniformity of the static magnetic field are controlled by the sequencer 104.

The sequencer 104 is for controlling operations of the parts constituting the MRI apparatus 100 as described above to implement the measurement, and it controls them so that the parts operate at timings and intensities stored in programs beforehand. Among the programs, in particular, a program describing timings and intensities of the radio frequency magnetic field, the gradient magnetic field and signal reception is called pulse sequence. The measurement is performed according to the pulse sequence and imaging parameters required for controlling it. The pulse sequence is prepared beforehand, and stored in the storage device 112, and the imaging parameters are inputted through a user interface by the operator.

Further, the computer 110 performs not only signal processing for processing the received signals, but also operational control of the whole MRI apparatus 100 etc. Furthermore, the computer 110 according to this embodiment constitutes an information processor with the storage device 112, and calculates a slice position to be recommended (recommended slice position) from an image for setting a slice position (scout image).

Figure 2:
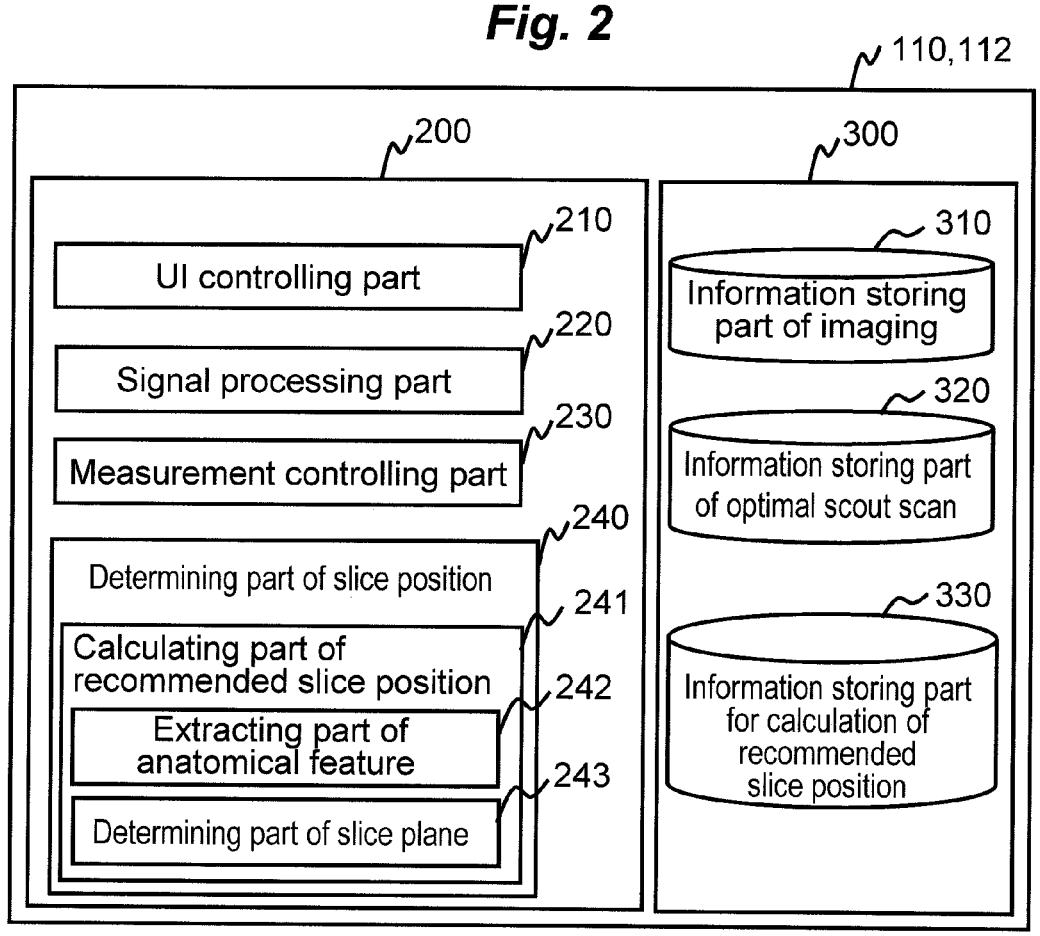
FIG. 2 is a functional block diagram of a computer according to the first embodiment.

A functional block diagram of an information processor constituted by the computer 110 and the storage device 112 according to this embodiment for implementing the above operation is shown in FIG. 2. As shown in this drawing, the information processor according to this embodiment is provided with a control part 200 and a storing part 300. The control part 200 is provided with a user interface (UI) controlling part 210, a signal processing part 220, a measurement controlling part 230, and a determining part of slice position 240. Further, the storing part 300 is for storing information required for various processing performed by the control part 200, and is provided with an information storing part of imaging 310, an information storing part of optimal scout scan 320, and an information storing part for calculation of recommended slice position 330.

Various kinds of information required for performing an examination with the MRI apparatus 100, for example, protocol, is registered at the information storing part of imaging 310. In an examination using the MRI apparatus 100, in general, scout scan for obtaining a scout image, preparation imaging for adjustment of uniformity of the static magnetic field and correction of coil sensitivity, and main scan for obtaining an image for diagnosis of the determined slice position are sequentially executed. Each imaging is constituted by one or more measurements, and each measurement is performed according to a pulse sequence and imaging parameters. The protocol defines order of the imaging, order of measurements within each imaging, and kind of measurement, and it is prepared by the operator in advance of execution of the examination, and stored. The protocol is created according to the examination region such as head, lumbar vertebra, knee and shoulder, or objective disease, and includes pulse sequences executed in each imaging and imaging parameters therefor.

Further, at the information storing part of imaging 310, pulse sequences used for preparation of the protocol, imaging parameters inputted by the operator, and so forth are registered. Examples of the pulse sequences to be registered include, for example, those for FSE (Fast Spin Echo), GrE (Gradient Echo), EPI (Echo Planar Imaging), etc., and examples of the imaging parameters include TR (repetition time), TE (echo time), FOV (field of view), slice thickness, number of slices, order of imaging for the case of imaging a plurality of slices, and so forth.

The protocol may be created by the operator through a user interface and registered at the information storing part of imaging 310 for every examination, or it may be created beforehand for every examination region and/or disease, and stored in the information storing part of imaging 310. In the latter case, the protocol is extracted by the operator from those stored for every examination, and determined. Further, optimal protocols correlated to specific examination regions may be stored in the information storing part of imaging 310, so that when the operator specifies the examination region at the time of setting the imaging parameters, a protocol stored as the protocol correlated to that examination region is extracted as initial values of the optimal protocol.

At the information storing part of optimal scout scan 320, there is registered optimal scout scan information defining optimal procedure for scout scan for every examination region, or for every examination region and every examination type when the examination includes examinations for a plurality of different slice positions for every examination region. Specifically, pulse sequences, imaging parameters used in the slice for scout scan to be imaged are registered, and when the imaging is performed for a plurality of slices, order of the imaging is registered. The optimal scout scan can be selected and set by the operator at the time of preparing the protocol. Alternatively, the optimal scout scan information may be contained in the initial values of the optimal protocol mentioned above.

At the information storing part for calculation of recommended slice position 330, information used for calculating a recommended slice position from a scout image is registered. For example, algorithms executed for generating a recommended slice position from a scout image according to the examination region are registered. Further, types of the image processing performed within the algorithms, positional relationships between anatomical feature according to the examination region such as anatomical feature used for calculation of the recommended slice position and the recommended slice position, and so forth are also registered. In addition, the positional relationship between the anatomical feature and the recommended slice position may be set by the operator.

In addition, in the case of a region for which a plurality of recommended slice positions can be set, positional relationships between the anatomical feature and the recommended slice position for every type of mark (OM line, intervertebral disc line etc.) and every examination type (routine examination, epilepsy examination, etc.) may be contained as a list of slice positions, so that the operator can select any one of them for each pulse sequence of the main scan. This allows setting of the slice position according to the operator's selection. In addition, a graphical interface (GI) displayed on the display 111 may be included, so that the operator can visually confirm the relationship between the slice position and the position of the anatomical landmark at the time of selection from the list of slice positions. Furthermore, input for adjustment of the position may be received through this GI.

Examples of the anatomical feature include, for example, mid-sagittal line, head contour, brain contour, corpus callosum, pons, brain stem, pituitary gland, and clivi for the case of the head as the examination region, inclination of spinal nerve, and position of intervertebral disc for the case of lumbar vertebra, positions of medial condyle of the femur, lateral condyle of the femur, femur, and tibia, line connecting medial condyle of femur and lateral condyle of femur, articular surface between femur and tibia for the case of knee, positions of supraspinous muscle, caput of bone, scapula, acromion, and clavicle, line parallel to supraspinous muscle, line along humerus, tangential line of articular surface between caput of bone and scapula, line connecting caput of bone and scapula for the case of shoulder, and so forth. These anatomical features are defined beforehand according to the examination region, and registered.

The UI controlling part 210 controls the user interface including the input device 116 and the display 111, and performs user interface processing such as presenting processing results to the operator and receiving input from the operator.

The signal processing part 220 performs processing of the echo signals obtained in the MRI apparatus 100 to reconstruct an image. Further, on the basis of the processing of the echo signals, it calculates control values required for imaging such as center frequency and RF irradiation intensity, and transmits them to the sequencer 104 of the apparatus.

The measurement controlling part 230 reads out a pulse sequence to be executed and imaging parameters to be used according to a protocol created by the operator and registered at the information storing part of imaging 310, and gives commands to the sequencer 104 to execute the measurement.

The determining part of slice position 240 determines the slice position for the main scan on the basis of a scout image. Further, the determining part of slice position 240 according to this embodiment is provided with a calculating part of recommended slice position 241 for calculating a recommended slice position from a scout image. The calculating part of recommended slice position 241 also is provided with an extracting part of anatomical feature 242 for extracting an anatomical feature defined beforehand on a two-dimensional image, and a determining part of slice plane 243 for determining a new slice plane using an anatomical feature on each of two two-dimensional images.

The calculating part of recommended slice position 241 calculates a recommended slice position according to the algorithm registered at the information storing part for calculation of recommended slice position 330 from a scout image obtained by the scout scan performed according to the optimal scout scan information.

The extracting part of anatomical feature 242 extracts the anatomical feature stored in the information storing part for calculation of recommended slice position 330 from a two-dimensional image such as a scout image by image processing stored in the information storing part for calculation of recommended slice position 330 according to the algorithm stored in the information storing part for calculation of recommended slice position 330.

The determining part of slice plane 243 determines a new slice plane crossing both the mutually crossing two slice planes by using the anatomical feature extracted from the image groups parallel to each of the two slice planes according to the algorithm stored in the information storing part for calculation of recommended slice position 330.

The computer 110 is equipped with CPU and a memory, and the functions of the control part 200 implemented by the computer 110 are realized by CPU by loading programs stored in the storage device 112 to the memory and executing them. Further, the storing part 300 is realized on the storage device 112. All or a part of the functions may be realized by an information processor as a general-purpose information processor that is independently provided from the MRI apparatus 100, and can transmit and receive data to or from the MRI apparatus 100. Similarly, a part or all of the storing part 300 may be realized by an external storage device that is independently provided from the MRI apparatus 100, and can transmit and receive data to or from the MRI apparatus 100.

Hereafter, the recommended slice position calculation processing performed by the calculating part of recommended slice position 241 according to the algorithm registered at the information storing part for calculation of recommended slice position 330 will be explained with reference to an example. This example relates to a case of routine examination of the head.

It is contemplated that, in a routine examination of the head, a T1 emphasized image, a T2 emphasized image, a FLAIR image, and a diffusion-weighted image are obtained in the main scan. A slice position is set to have an orientation perpendicular to the mid-sagittal plane and parallel to the OM line, and is set in a region covering all the brain. The OM line is a line connecting the root of nose and the lower end of the pons on the image of the mid-sagittal plane, and it is a line more easily recognized in an image of a plane closer to the mid-sagittal plane. Therefore, the slice position is determined on an image of mid-sagittal plane.

Figure 3A:
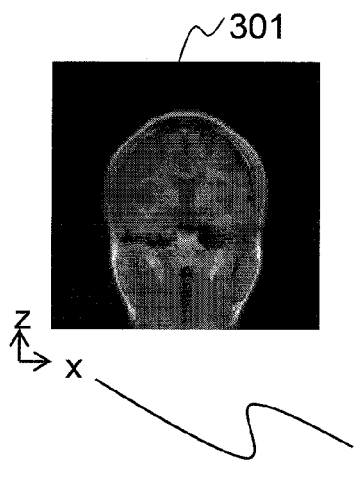
FIG. 3A shows an example of scout image according to the first embodiment.
Figure 3B:
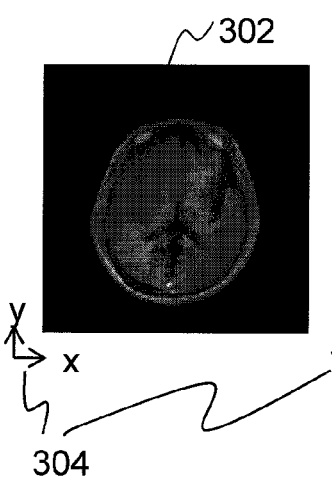
FIG. 3B shows an example of scout image according to the first embodiment.
Figure 3C:
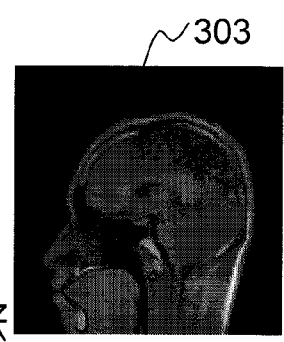
FIG. 3C shows an example of scout image according to the first embodiment.

Therefore, as optimal scout scan information for routine examination of the head, that enabling determination of the mid-sagittal plane and acquisition of an image of mid-sagittal plane is registered at the information storing part of optimal scout scan 320. For example, it is registered so that by using a pulse sequence of the GrE (gradient echo) type for T1 emphasis, imaging is performed for a plurality of slices parallel to the coronal plane, the axial plane, and the sagittal plane in this order. Although the number of the slices used here is not limited, an example in which imaging is performed for five slices is explained below. Examples of the scout image obtained by using such a pulse sequence are shown in FIG. 3A, FIG. 3B, and FIG. 3C. FIG. 3A is an image 301 of a slice parallel to the coronal plane (coronal image), FIG. 3B is an image 302 of a slice parallel to the axial plane (axial image), and FIG. 3C is an image 303 of a slice parallel to the sagittal plane (sagittal image). The imaging parameters used for this case are TR/TE of 30/1.5, FOV of 270, FA of 45, pixel numbers of 128×128, and slice thickness of 10 mm. The axes of the coordinates 304 are shown at the lower left of each image. Hereafter, in this specification, the body axis direction is the z-axis direction, and the subject 103 is horizontally placed on the table 115. And among the two directions perpendicular to the z-axis, the direction parallel to the horizontal plane is the x-axis direction, and the direction perpendicular to the horizontal plane is the y-axis direction.

Further, at the information storing part for calculation of recommended slice position 330, there are registered algorithms for determining the mid-sagittal plane from the coronal image and the axial image, creating an image of the mid-sagittal plane from the sagittal image, and calculating a recommended slice position on that image of the mid-sagittal plane. The mid-sagittal line and head contour, brain contour, corpus callosum, pons, brain stem, pituitary gland, and clivi on the image of mid-sagittal plane are registered as anatomical features, and as image processing, that for extracting the mid-sagittal line from each scout image, and that for specifying a recommended slice position on the image of the mid-sagittal plane are registered.

The flow of the recommended slice position calculation processing performed in the routine examination of the head by the calculating part of recommended slice position 241 according to the algorithms registered at the information storing part for calculation of recommended slice position 330 is shown in FIG. 4. The extracting part of anatomical feature 242 calculates slope of the mid-sagittal line on the coronal image (Step S401). Then, the calculating part of recommended slice position 241 determines the position of the axial image suitable for the image processing on the coronal image (Step S402). And the extracting part of anatomical feature 242 calculates the position of the mid-sagittal line on the axial image at the position determined in Step S402 (Step S403). And the determining part of slice plane 243 determines the mid-sagittal plane from the slope of the mid-sagittal line obtained in Step S401, and the mid-sagittal line obtained in Step S402 (Step S404).

Then, the calculating part of recommended slice position 241 analyzes validity of the mid-sagittal plane obtained in Step S404 with reference to the sagittal image (Step S405), and when it is judged to be valid (Step S406), it creates an image of mid-sagittal plane from the sagittal image (Step S407). And the calculating part of recommended slice position 241 specifies a recommended slice position on the image of mid-sagittal plane (Step S408) to complete the processing. On the other hand, when it is judged to be invalid in Step S406, the processings of Step S407 and thereafter are not performed to complete the processing.

Figure 5A:
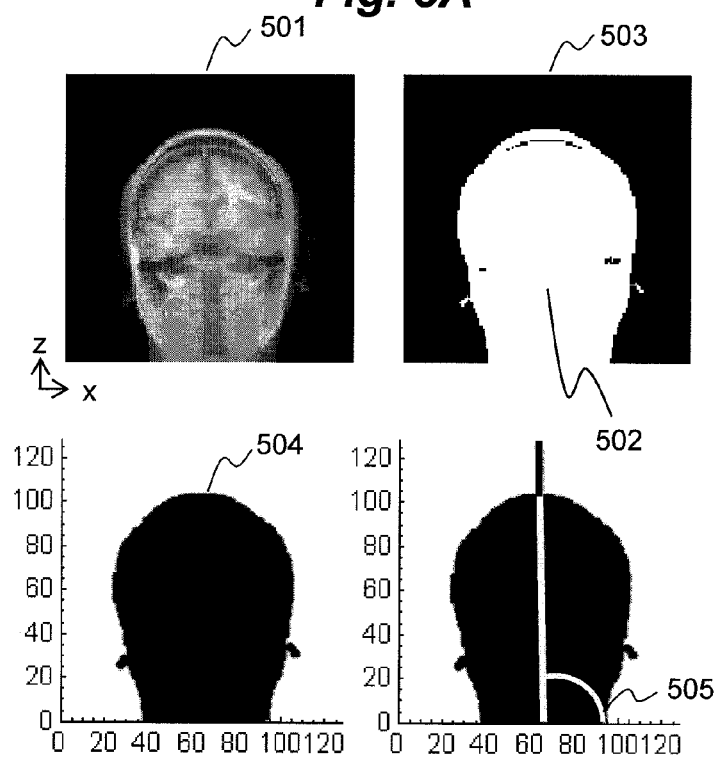
FIG. 5A includes drawings for explaining coronal mid-sagittal line calculation processing according to the first embodiment.

The details of each image processing in the recommended slice position calculation processing will be explained below. The procedures of each of these image processing are registered beforehand at the information storing part for calculation of recommended slice position 330. First, the processing for calculating slope of the mid-sagittal line on the coronal image performed by the extracting part of anatomical feature 242 in Step S401 (henceforth referred to as coronal mid-sagittal line calculation processing) is explained. FIG. 5A includes drawings for explaining the coronal mid-sagittal line calculation processing according to this embodiment.

In the coronal mid-sagittal line calculation processing, approximate slope of the mid-sagittal line is calculated. First, all of the obtained five coronal images are added to create an added image 501. And a binarization processing is performed by using a threshold value, and a head region 502 and a background region 503 are separated on the added image 501. In the above processing, as the threshold value, for example, an average of pixel values of all the pixels on the added image or the like is used. A region of pixels having a value not smaller than the threshold value is defined as the head region 502, and a region of pixels having a value smaller than the threshold value is defined as the background region 503.

Then, the pixel coordinates in the head region 502 are extracted, values of the coordinates are plotted (504), and least square fitting is performed with a linear function. A slope 505 of the linear function obtained by this fitting is considered as the approximate slope of the mid-sagittal line on the coronal image. This procedure is based on the fact that the shape of the head is substantially symmetrical on the coronal plane, and is not influenced by contrast of the image.

However, the coronal mid-sagittal line calculation processing is not limited to the above processing. Various kinds of techniques for image processing can be used. For example, an evaluation function can be created on the basis of a combination of pixel values and differential values of pixels to calculate the mid-sagittal line and determine the slope.

Figure 5B:
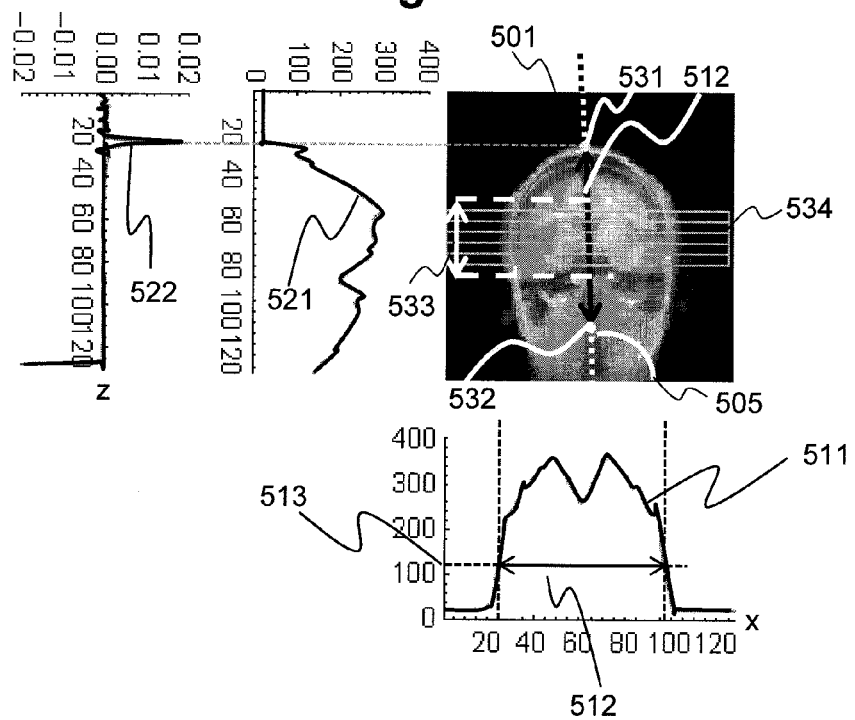
FIG. 5B includes drawings for explaining axial image determination processing according to the first embodiment.

Hereafter, with reference to FIG. 5B, the processing for determining position of an axial image suitable for the image processing performed by the calculating part of recommended slice position 241 in Step S402 (axial image determination processing) will be explained. In this processing, the added image 501 shown in FIG. 5A is used.

First, one-dimensional projection images 511 and 521 of the added image 501 on the x-axis and the z-axis, respectively, are created. And from the one-dimensional projection image 511 on the x-axis, the head is defined, and the x-coordinates of the both ends of the head and the width 512 between them are determined. The x-coordinates and the width 512 are calculated by a threshold value processing. That is, in the one-dimensional projection image 511, a group of the pixels having a pixel value not smaller than the threshold value 513 is determined to indicate the width 512 of the head. As the threshold value 513, a value determined by a procedure defined beforehand, such as an average of the pixel values of all the pixels on the added image 501, is used.

As for the one-dimensional projection image 521 on the z-axis, a differential value 522 of the reciprocal thereof is calculated, and the point giving the maximum value thereof is obtained to determine the z-coordinate of the vertex 531. And the x-coordinate of the vertex 531 is the x-coordinate of the middle point of the x-coordinates of the both ends of the head. Then, on this added image 501, coordinates of a point 532 at a distance of the width 512 from the vertex 531 along the slope of the mid-sagittal line determined by the aforementioned coronal mid-sagittal line calculation processing are calculated. An axial image of a slice plane within a predetermined range between the vertex 531 and the point 532 is chosen as an axial image suitable for the image processing. As for the predetermined range, for example, one or more axial images obtained in the region 533 between the position of L/4 and the position of 3L/4 from the vertex 531 are chosen, wherein L is the distance between the vertex 531 and the point 532 (head width 512). For the selection of the axial images, the slice positions 534 of the slice planes parallel to the axial planes for which the five axial images are obtained, which are registered beforehand as imaging parameters.

Figure 6A:
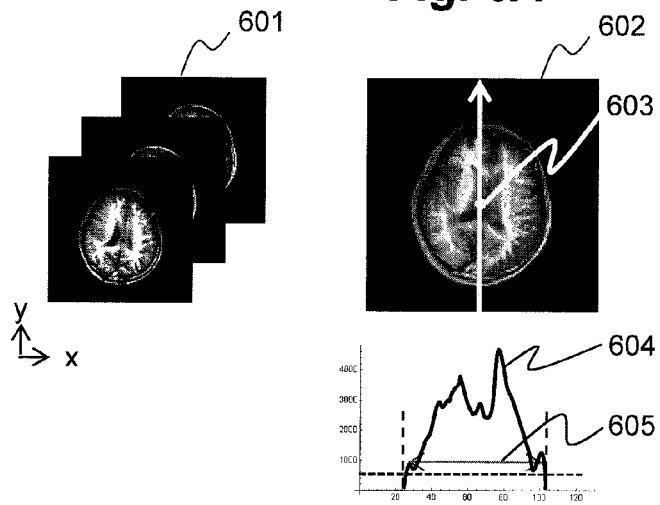
FIG. 6A includes drawings for explaining axial mid-sagittal line calculation processing according to the first embodiment.
Figure 6B:
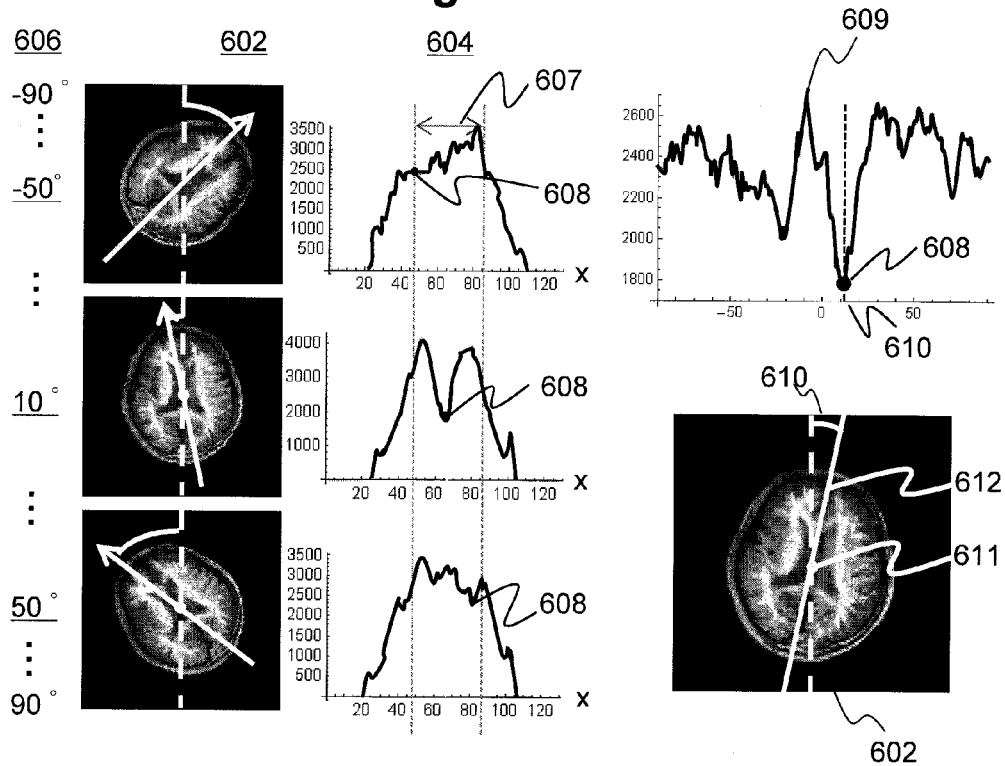
FIG. 6B includes drawings for explaining axial mid-sagittal line calculation processing according to the first embodiment.
Figure 6C:
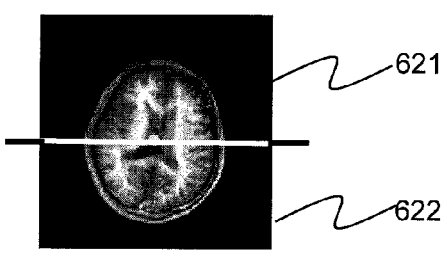
FIG. 6C includes a drawing for explaining axial mid-sagittal line calculation processing according to the first embodiment.

The processing for calculating the position of the mid-sagittal line on the axial image performed by the extracting part of anatomical feature 242 in Step S403 (axial mid-sagittal line calculation processing) will be explained below. FIG. 6A, FIG. 6B, and FIG. 6C include drawings for explaining the axial mid-sagittal line calculation processing. As shown in FIG. 6A, in an axial image selected by the axial image selection processing, a binarization processing is performed by using a threshold value in the same manner as that used in the aforementioned coronal mid-sagittal line calculation processing to separate a head region and a background region. Further, the region defined as the head region is divided into two or more of groups according to size of the pixel value. A gradation corrected image 601 assigned with a certain value of pixel value is created for each group, i.e., such images are created in the number of the groups. By the processing for creating the gradation corrected images 601, large pixel values of the region of blood vessel, fat or the like can be smoothened. Then, the gradation corrected images 601 are added to create an added image 602.

Then, in the added image 602, the center of gravity 603 of the image is calculated. The center of gravity 603 is calculated by a generally used procedure for image processing. For example, there is used a method of calculating it with weighting according to the pixel values, a method of calculating it only with coordinates on the assumption that the pixels in the region extracted as the head region in the added image 602 have the same pixel values, or the like.

Then, a one-dimensional projection image 604 on the x-axis of the added image 602 is created, and the width 605 of the head and the x-coordinates of both ends are determined by using a threshold value in the same manner as that used in the axial image selection processing.

Then, as shown in FIG. 6B, the added image 602 is rotated around the center of gravity 603 as the center by a unit defined beforehand in a range of −90 degrees to +90 degrees on both sides of a reference line defined beforehand, and a one-dimensional projection image 604 on the x-axis is created for every angle 606 with respect to the reference line. The reference line may be, for example, the y-axis. In each projection image 604, there are extracted x-coordinate of a point 608 at which luminance is minimized in the range of a width 607, which is ½ of the width 605 of the head, on both sides of the middle point between the x-coordinates of the both ends of the head as the center, and luminance at that point. And the extracted luminance and the corresponding angle 606 of the projection image 604 are correlated and plotted as a plot 609.

From the plot 609, the angle 606 at which the luminance of the point 608 is minimized is specified in each projection image 604. This angle is defined as the inclination α 610 of the mid-sagittal line on the axial image. By using the x-coordinate Xmin of the point 608 at which the luminance is minimized and the coordinates (X0, Y0) of the center of gravity on the one-dimensional projection image 604 at that inclination, the coordinates (XP, YP) of the point P611 at which the mid-sagittal plane passes are calculated according to the following equation (1).

$$XP = X0 - (Xmin - X0) \times \cos \alpha$$

$$YP = Y0 - (Xmin - X0) \times \sin \alpha \quad (1)$$

A straight line passing the point P611, of which inclination is the angle α 610, is defined as the mid-sagittal line 612 in the axial image.

The above axial mid-sagittal line calculation processing is a processing utilizing the fact that pixel values of pixels in a region corresponding to the mid-sagittal line on the axial image (henceforth simply referred to as pixel values of the mid-sagittal line, the same shall apply to the other cases) are lower than the pixel values of the pixels in the surrounding brain parenchyma region. In contrast, when the pixel values of the region of the mid-sagittal line become higher than the pixel values of the region of brain parenchyma, a processing for calculating values providing high luminance value in the one-dimensional projection image is performed.

Further, in the aforementioned axial mid-sagittal line calculation processing, the size of the pixel value was used as an evaluation function. However, the evaluation function is not limited to this. For example, edge information obtained by differentiating the one-dimensional projection image 604 may be used. Alternatively, information on standard deviation of the one-dimensional projection image 604 may be used. Furthermore, the processing may be performed with a complex of these. With such a complex, more accurate mid-sagittal line extraction is enabled.

When the axial image is obtained at a position close to the brain lower part, another method may be used for the mid-sagittal line extraction. That is, as shown in FIG. 6C, the axial image is divided into a region 621 on the anterior wall side, and a region 622 on the posterior wall side with a line passing through the center of gravity and parallel to the x-axis. Then, total of the pixel values of the pixels in the region 621 on the anterior wall side is calculated, the image is rotated around the center of gravity as the center by a unit defined beforehand in a range of −90 degrees to +90 degrees on both sides of a reference line defined beforehand, and total of the pixel values is calculated for every rotation by the rotation unit. A rotation angle giving a minimum calculated total is defined as the slope of the mid-sagittal line, and the center of gravity is defined as a point through which the mid-sagittal plane passes. This procedure is based on the fact that in an axial image at a position close to the lower part of the brain, pixel values of nasal cavity region are small, and pixel values of eyeball and cerebellum regions are large. Further, it also based on the fact that in an axial image at a position close to the lower part of the brain, the mid-sagittal plane substantially passes the center of gravity regardless of the inclination of the head. In addition, whether an axial image is an image at a position close to the lower part of brain can be determined on the basis of the position of the axial image. For example, when the selected axial image is one of the first to third images counted from the vertex side, it can be judged that the image is an image close to the lower part of the brain.

An example of the processing was described above, and the method for extracting the position of the mid-sagittal line is not limited to the above processing. As other methods, there are mentioned a method of calculating the mid-sagittal line by creating an evaluation function based on a combination of pixel values or differential values of pixels, and so forth.

Figure 7A:
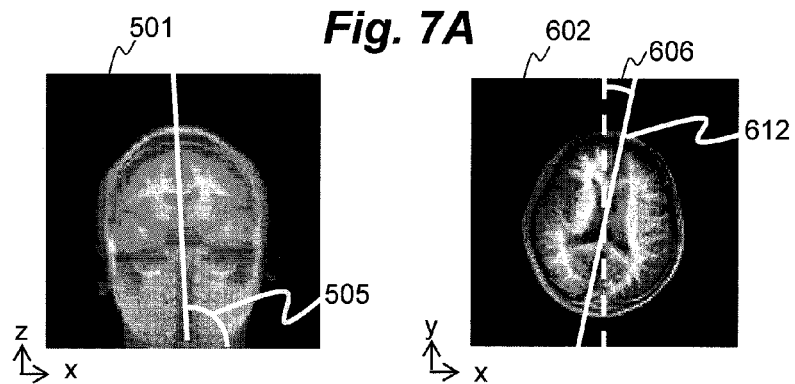
FIG. 7A includes drawings for explaining mid-sagittal plane determination processing according to the first embodiment.
Figure 7B:
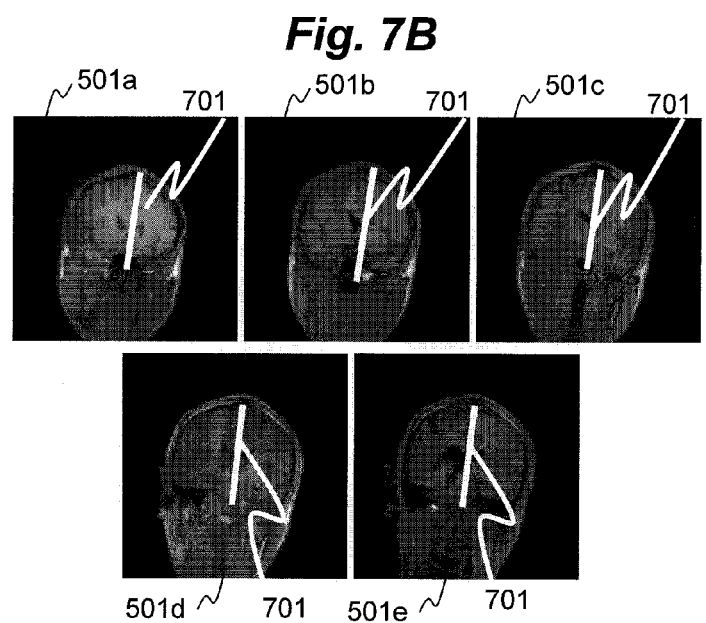
FIG. 7B includes drawings for explaining mid-sagittal plane determination processing according to the first embodiment.
Figure 7C:
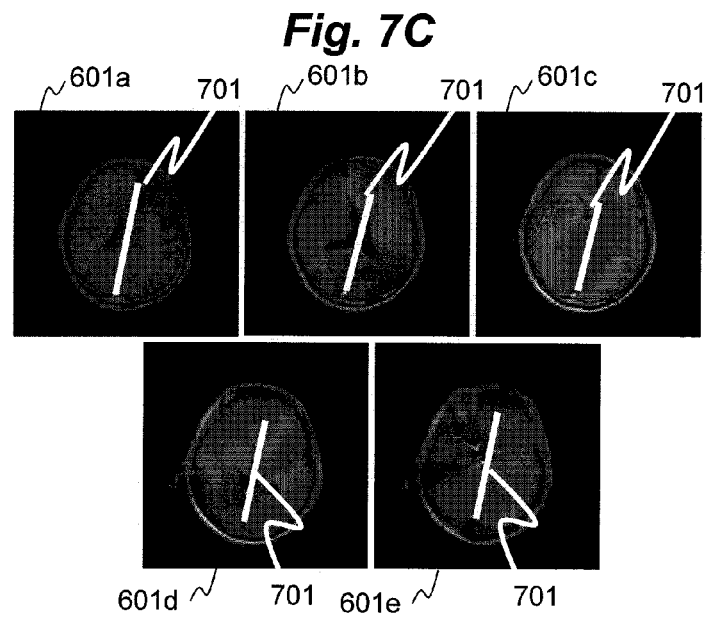
FIG. 7C includes drawings for explaining mid-sagittal plane determination processing according to the first embodiment.

Hereafter, the mid-sagittal plane determination processing for determining the mid-sagittal plane from the slope of the mid-sagittal line on the coronal image and the position of the mid-sagittal line on the axial image performed by the determining part of slice plane 243 in Step S404 will be explained. FIG. 7A, FIG. 7B and FIG. 7C include the drawings for explaining this mid-sagittal plane determination processing.

As shown in FIG. 7A, from the slope 505 of the mid-sagittal line on the coronal image 501 determined by the coronal mid-sagittal line calculation processing and the mid-sagittal line 612 on the axial image 602 determined by the axial mid-sagittal line calculation processing, the initial position of the mid-sagittal plane is determined. That is, a plane having the slope 505 of the mid-sagittal line on the coronal image 501 and including the mid-sagittal line 612 on the axial image 602 is considered as the initial position of the mid-sagittal plane (initial mid-sagittal plane). And as shown in FIG. 7B and FIG. 7C, lines of intersection 701 of the initial mid-sagittal plane with the five coronal images 501a, 501b, 501c, 501d and 501e and the five axial images 601a, 601b, 601c, 601d and 601e obtained by the scout scan are obtained.

Then, the pixel values on the lines of intersection 701 are made into an evaluation function, and the orientation and the position of initial mid-sagittal plane are changed and adjusted so as to minimize the value of the evaluation function. And a plane of the orientation and the position giving the minimum value of the evaluation function is defined as the mid-sagittal plane. For the adjustment, for example, the least square method and so forth are used. Further, the evaluation function may be combined with first degree differentiation or second degree differentiation of pixel values, and so forth. The extraction accuracy can be thereby improved. Furthermore, in order to improve the accuracy of the evaluation, the lines of intersection 701 are desirably lines of intersection substantially only in the brain region. The brain region is defined as, for example, on the coronal image, a region between the vertex 531 and the point 532, or in the axial image, a region of a circle having the center at the center of gravity and a diameter of the width 605 of the head. Moreover, a coronal image and an axial image may be separated into a signal region and a background region, respectively, by a binarization processing using respective average of pixel values as a threshold, and the signal region may be defined as the brain region.

Hereafter, the image of mid-sagittal plane creation processing for creating an image of mid-sagittal plane from the sagittal image performed by the calculating part of recommended slice position 241 in Step S407 mentioned above will be explained. First, by using the pixel values of the five sagittal images obtained by the scout scan, pixel values of the mid-sagittal plane determined in Step S404 are calculated by interpolation. For this calculation, as the positions of the five sagittal images, those set as the slice positions of the five slices parallel to the sagittal plane at the time of the scout scan as the imaging parameters are used.

When there is an image in which 70% or more of the head region is included in the mid-sagittal plane among the five sagittal images, the slice position of this image may be used as the mid-sagittal plane. With such a configuration, the processing time can be shortened.

Hereafter, the slice specifying processing for specifying a recommended slice position on the image of mid-sagittal plane created by the calculating part of recommended slice position 241 in Step S408 mentioned above will be explained. In this processing, positions of anatomical landmarks on the image of mid-sagittal plane are automatically recognized, and a slice position is determined according to the information on the relation of the positions of the anatomical landmarks and slice position defined beforehand.

First, the procedure for automatically recognizing the anatomical landmarks on the image of mid-sagittal plane will be explained. The automatic recognition is attained by a fitting processing using a template model that can change according to the individual difference of shape. The template model to be used is constituted by a plurality of points, and each point corresponds to an anatomical landmark on the image of mid-sagittal plane. This template model is fitted to the image of mid-sagittal plane, positions of the points constituting the template model are calculated, and the positions of the anatomical landmarks on the image of mid-sagittal plane are extracted.

Figure 8A:
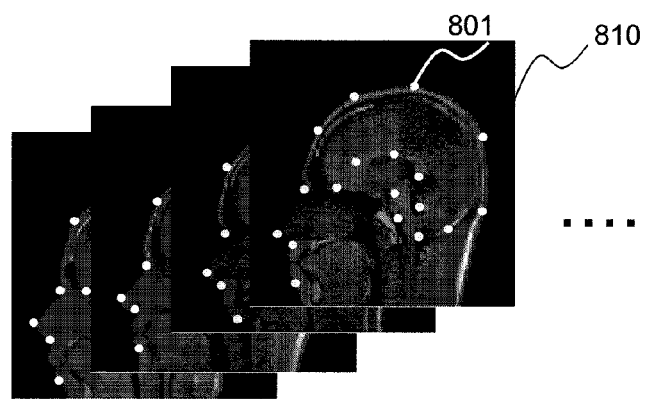
FIG. 8A includes drawings for explaining a procedure for creating a template model according to the first embodiment.
Figure 8B:
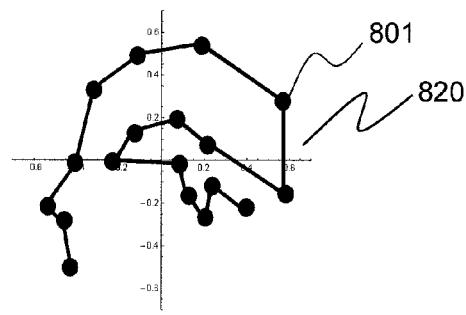
FIG. 8B includes a drawing for explaining a procedure for creating a template model according to the first embodiment.
Figure 8C:
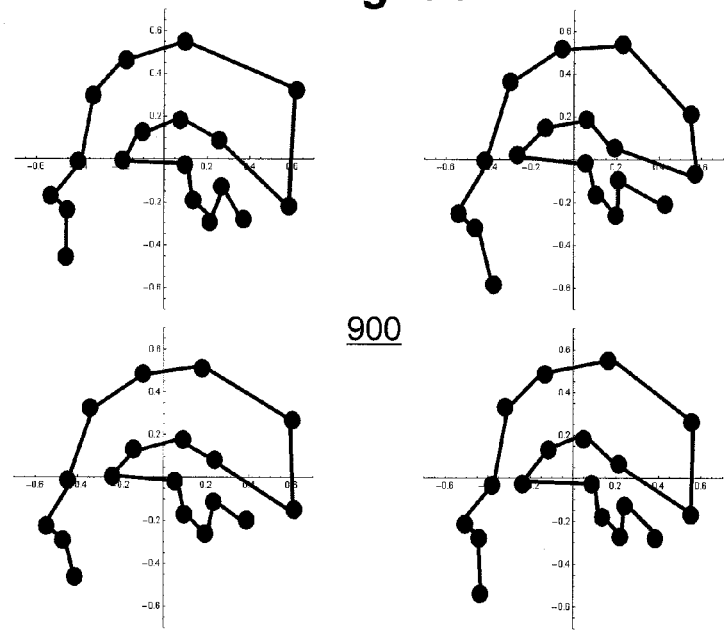
FIG. 8C includes drawings for explaining a procedure for creating a template model according to the first embodiment.

First, the procedure for creating the template model 800 to be used will be explained with reference to FIG. 8A, FIG. 8B, and FIG. 8C. First, image of mid-sagittal planes 810 of a plurality of subjects are obtained. In these image of mid-sagittal planes 810, coordinates of a plurality of anatomical landmarks (landmarks) 801, such as those of head contour, borders of corpus callosum, infracerebral edge, pituitary gland, clivi, pons, oblongata, and cerebellum inferior border, are extracted. The subjects used here are preferably healthy subjects, and the number of the subjects is preferably proportional to the number of the landmarks 801 to be extracted. Size and inclination of distribution of the extracted landmarks 801 of each subject are standardized by rotation, scaling, and parallel translation. As for the positions of the standardized landmarks 801, averages are calculated for a plurality of the subjects, and used as a standard model 820 as shown in FIG. 8B.

Then, the coordinates of all the landmarks 801 of the subjects and the standard model 820 are made into one-dimensional vectors, a variance covariance matrix is prepared, and then the eigenvalue and eigenvector of the matrix are calculated. The eigenvector calculated above is a vector of a direction along which individual difference is observed in the distribution of the landmarks 801 of the subjects. When the eigenvector is represented by Pi (i=1, ..., N, N depends on the matrix number of the variance covariance matrix), and the one-dimensional vector of the standard model 820 is represented by $X_{VC}$, one-dimensional vector X of the template model in which change tendency of individual difference is represented with a parameter is represented by the following equation (2).

$$X = X_{VC} + \sum_{i=1}^{N} b_i P_i \qquad (2)$$

In this equation, b is a parameter for determining size of change. As described above, this standard model 820 can be fitted to the individual difference of the shape by adjusting the value of b. As shown in FIG. 8C, the template model 800 is obtained by adjusting the value of b to change the shape of the standard model 820.

The value of b can be set arbitrarily. For example, when the eigenvalue is represented by $\lambda_i$, the range of b may be the range represented by the following equation (3).

$$-3\sqrt{\lambda_i} < b_i < 3\sqrt{\lambda_i} \qquad (3)$$

As described above, by limiting the value of b, when the standard model 820 is changed to create the template model 800, it can be prevent from significantly deviating from the original shape. Further, since an eigenvector having a larger eigenvalue tends to show a larger individual difference, only an eigenvector having a large eigenvalue may be included in the standard model 820. With such a configuration, calculation time can be shortened.

Further, as the template model 800 to be used, a template model of a fixed shape may be used by ignoring individual difference. An approximate position can be thereby calculated at high speed.

In addition, the template model 800 is created by the operator using the standard model 820 registered beforehand at the information storing part for calculation of recommended slice position 330. Further, it may be created beforehand and stored in the information storing part for calculation of recommended slice position 330. The template model 800 may be created for every race, sex, age and so forth, and stored. More precise characteristic extraction is thereby enabled. When a plurality of template models 800 are prepared, they may be held with being correlated with any type of information registered at the time of examination as information of a subject, and one of them may be automatically set at the time of examination, or an interface with which the operator can choose the template model 800 to be used may be provided. The template model 800 to be used may be made freely replaceable at any time.

Figure 9A:
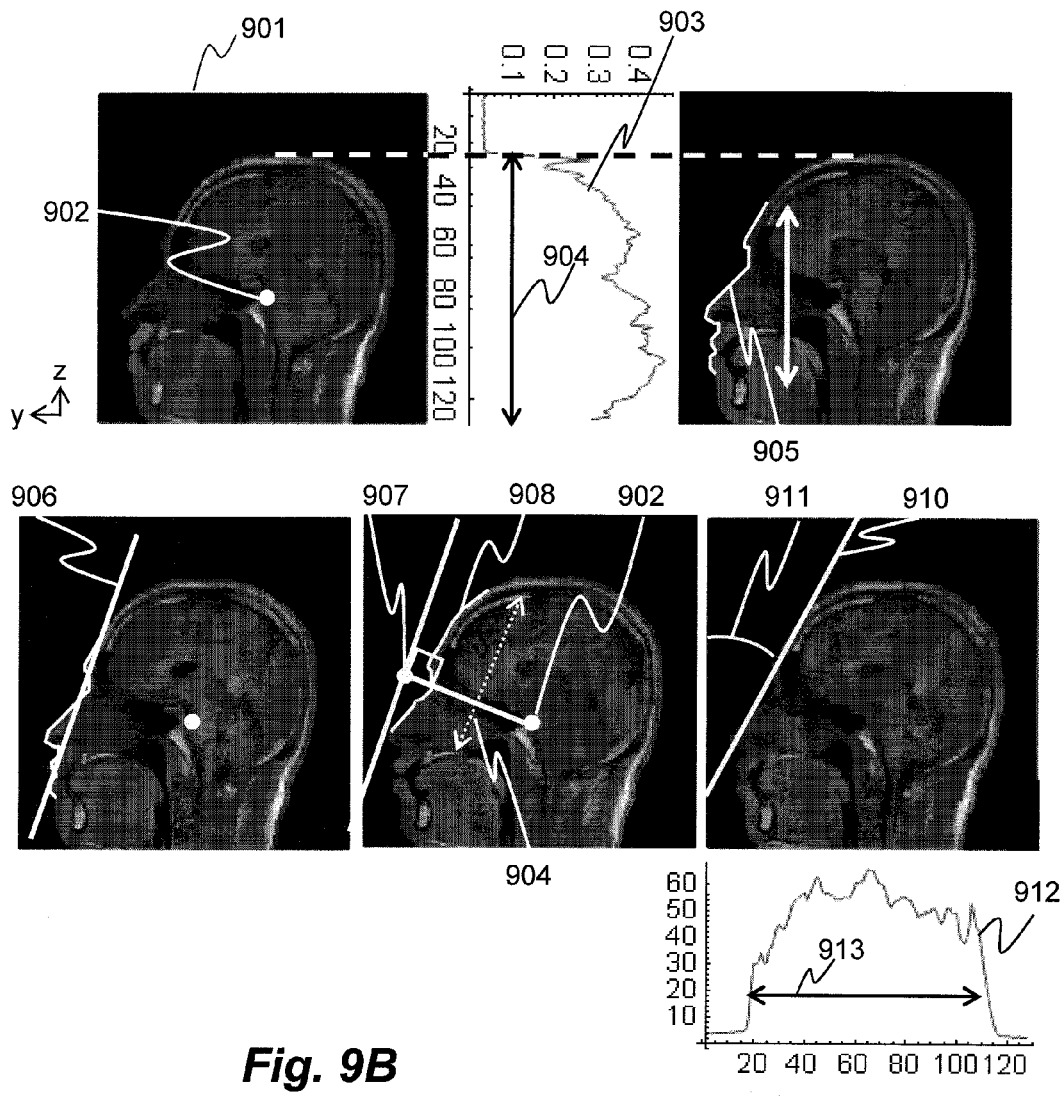
FIG. 9A includes drawings for explaining fitting of a template model according to the first embodiment.
Figure 9B:
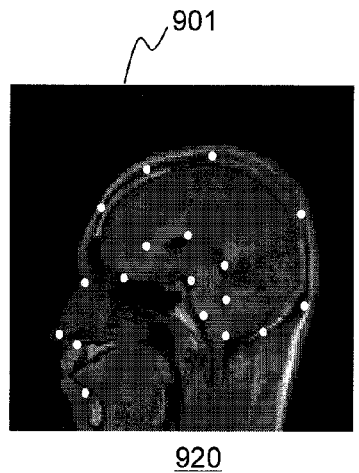
FIG. 9B includes drawings for explaining fitting of a template model according to the first embodiment.

The initial disposition for carrying out the fitting with the aforementioned template model 800 will be explained below with reference to FIG. 9A and FIG. 9B. First, as shown in FIG. 9A, the center of gravity 902 of an image of mid-sagittal plane 901 is calculated. Then, a one-dimensional projection image 903 on the z-axis is prepared, and a length 904 of the head is calculated in the obtained one-dimensional projection image 903. In the region defined by the length 904 of the head around the center of gravity 902 as the center, coordinates 905 of the contour on the anterior wall side are extracted by a threshold value processing. The extracted contour coordinates 905 are fitted with a linear function 906 by the least square method. Then, an altitude is drawn down from the center of gravity 902 to the obtained linear function 906, and in the region defined by the length 904 of the head around the intersection 907 with the altitude as the center, coordinates 908 of the contour on the anterior wall side are extracted again by a threshold value processing. Furthermore, the extracted coordinates 908 of the contour are fitted again with a linear function 910 by the least square method to obtain a slope 911. The slope 911 of the linear function 910 may also be obtained by a method of extracting coordinates of the head region by a threshold value processing, and fitting them with a linear function, or the like. Then, a one-dimensional projection image 912 on the y-axis is created, and the width 913 of the head is calculated by a threshold value processing. As shown in FIG. 9B, when the template model 800 is disposed at the original position 920 on the image of mid-sagittal plane, it is disposed at such a position that it is close to the corresponding landmarks 801 on the image of mid-sagittal plane on the basis of the center of gravity 902, the slope 910, and the width 904 of the head obtained as described above.

The procedure for fitting the template model 800 disposed at the aforementioned original position 920 with the image of mid-sagittal plane will be explained below. For the fitting, the position is renewed little by little from the original position 920 so that the landmarks 801 as points constituting the template model 800 are converged to the anatomical landmarks of the corresponding tissue on the image of mid-sagittal plane. Specifically, for each landmark 801, a processing for searching for a renewed point to which the landmark 801 should move, and changing the whole template model 800 by the least square method is repeatedly performed. The renewed point is determined by making pixel values on a straight line in the searching direction into an evaluation function, and searching for a specific point on the evaluation function. The searching direction and the searching width are determined according to the tissue having the characteristic points. In the case of the head, for the fitting, a processing for searching for a renewed point and changing the template model by rotation, scaling and parallel translation is first repeated for points on the contour of the head, and then a processing for searching for a renewed point and changing the template model by rotation, scaling and parallel translation is repeated for all the points in the template model 800. Finally, a processing for changing the model is repeated for all the points in the template model 800 with adding change based on a parameter indicating individual difference.

Figure 10A:
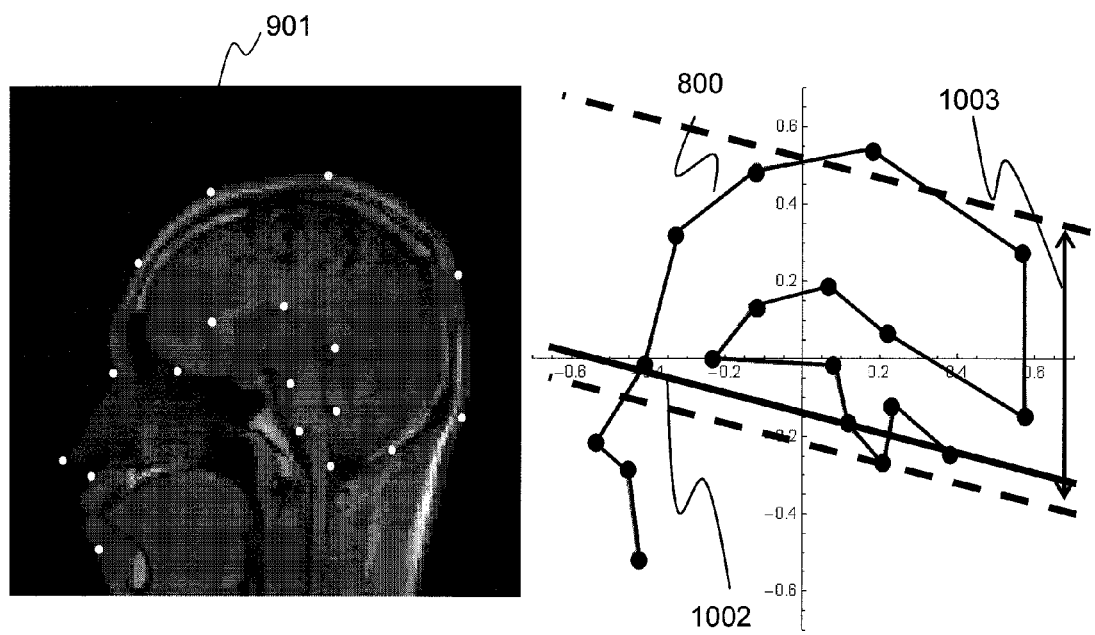
FIG. 10A includes drawings for explaining a procedure for calculating a recommended slice position from a template model according to the first embodiment.

By these processings, the landmarks 801 constituting the template model 800 are converged to the corresponding anatomical landmarks on the image of mid-sagittal plane 901 for which the processings are executed, as shown in FIG. 10A. And the coordinates of the landmarks 801 of the template model 800 in the above case are the coordinates of the anatomical landmarks required for determining a slice position. In this way, the anatomical landmarks on the image of mid-sagittal plane are automatically recognized. Then, according to the positional relationship of the anatomical feature and a recommended slice position registered at the information storing part for calculation of recommended slice position 330, the anatomical landmarks required for determining a recommended slice position are extracted, and a recommended slice position is determined. For example, in the case of the head, points of defining root of nose, pons, head contour, brain contour, corpus callosum and brain stem, and so forth are registered as the anatomical feature, the inclination of the OM line 1002 connecting the root of nose and the lower end of pons is registered as the orientation of the recommended slice position, and the range 1003 of the total brain is registered as the region of recommended slice position. On the basis of the above, as shown in FIG. 10B, the orientation 1004 and the region 1005 of the recommended slice position are determined from the positions of the landmarks 801 of the template model 800 subjected to the fitting on the image of mid-sagittal plane.

Figure 10B:
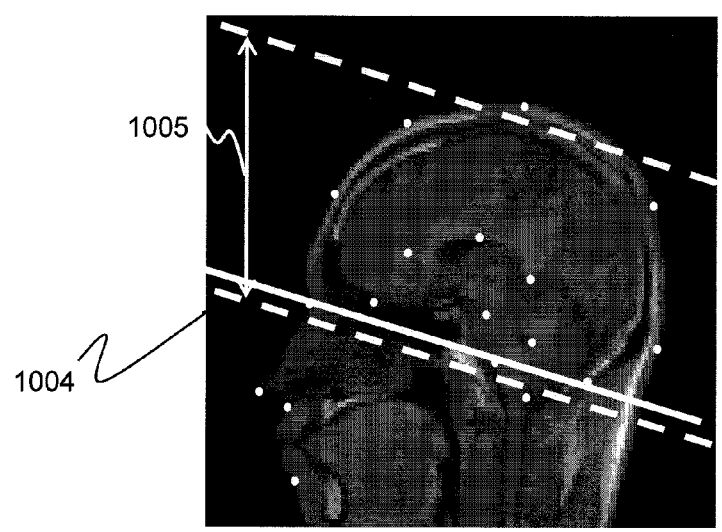
FIG. 10B includes a drawing for explaining a procedure for calculating a recommended slice position from a template model according to the first embodiment.

Although FIG. 10A and FIG. 10B show the imaging region only for the up-and-down direction, the positional information on the imaging region for the anterior-posterior direction can also be obtained in a similar manner. Further, although orientation of a plane parallel to the OM line is determined above as the orientation of the recommended slice position, the orientation of the recommended slice position is not limited to that. For example, in the case of examination of the head, the inclination of the AC-PC line connecting the commissurae anterior on the image of mid-sagittal plane, a line parallel to the brain stem, and so forth may be registered as orientation of recommended slice position.

Explained above is the recommended slice position calculation processing performed by the calculating part of recommended slice position 241 according to the algorithms registered at the information storing part for calculation of recommended slice position 330. Hereafter, the flow of the measurement preparation processing from the scout scan starting operation to the main scan starting operation according to this embodiment, in which the above recommended slice position calculation processing is incorporated, will be explained with reference to a specific example. As in the previously explained recommended slice position calculation processing, routine examination of the head is explained as an example. FIG. 11, FIG. 12A, FIG. 12B, FIG. 13A and FIG. 13B include charts for explaining the measurement preparation processing according to this embodiment, among which FIG. 11 is a chart for explaining the flow of the scout scan, and FIG. 12A, FIG. 12B, FIG. 13A and FIG. 13B are charts for explaining the flow of the processing after the scout scan. In this explanation, operations of the operator, processings executed by the computer 110, and operations of the sequencer 104 are explained, respectively. The protocol for the routine examination of the head is as follows: the scout scan is performed, then preparation imaging is performed with a pulse sequence for obtaining data for shimming and sensitivity map correction, and the main scan is performed for the slice position determined on the basis of the results of the scout scan.

If the operator gives an instruction for starting the scout scan via the input device 116 (Step S1101), the UI controlling part 210 receives the instruction from the operator in the computer 110. And the measurement controlling part 230 outputs a command to the sequencer 104 according to a pulse sequence and imaging parameters stored in the information storing part of optimal scout scan 320 as the optimal scout scan information (Step S1201). The sequencer 104 operates the respective parts according to the instruction from the computer 110 to start the scout scan (Step S1301), successively perform measurement for the coronal plane, the axial plane, and the sagittal plane in this order, and transmit the echo signals obtained in each measurement to the computer 110 in order (Steps S1302, S1303, S1304).

In the computer 110, when the echo signals obtained by the measurement for the coronal plane are received, the signal processing part 220 reconstructs an image to obtain a coronal image (Step S1202). And on the obtained coronal image, the calculating part of recommended slice position 241 calculates slope of the mid-sagittal line (Step S1203). Further, the calculating part of recommended slice position 241 determines the position of the axial image suitable for the image processing on the coronal image (Step S1204). The calculating part of recommended slice position 241 according to this embodiment executes the processings up to Step S1204, before the measurement for the axial plane is completed by the measurement controlling part 230.

Then, in the computer 110, when the echo signals obtained by the measurement for the axial plane are received, the signal processing part 220 reconstructs an image to obtain an axial image (Step S1205). And the calculating part of recommended slice position 241 specifies the mid-sagittal line on the axial image at the position determined in Step S1204 among the obtained axial images (Step S1206). And the calculating part of recommended slice position 241 specifies the mid-sagittal plane from the slope of the mid-sagittal line on the coronal image calculated in Step S1204, and the position of the mid-sagittal line on the axial image calculated in Step S1206 (Step S1207). The calculating part of recommended slice position 241 according to this embodiment executes processings up to Step S1207, before the measurement for the sagittal plane is completed by the measurement controlling part 230.

In the computer 110, when the echo signals obtained by the measurement for the sagittal plane are received, the signal processing part 220 reconstructs an image to obtain a sagittal image (Step S1208). In this case, the UI controlling part 210 displays the reconstructed scout images (coronal image, axial image, and sagittal image) as well as an indication for receiving an instruction for whether the scout scan is performed again or not on the display 111 (Step S1209). The operator confirms the scout images displayed on the display 111 (Step S1102), and gives an instruction for whether the scout images should be retaken or not (Step S1103). In the computer 110, the calculating part of recommended slice position 241 analyzes and judges validity of the mid-sagittal plane obtained in Step S1207 with referring to the sagittal image (Step S1210). As for the instruction for whether the scout images should be retaken or not, for example, the UI controlling part 210 displays operation buttons for receiving instructions for retaking and continuing the processing together with the scout images on the display 111, and receives the instruction through selection of them by the operator or the like.

In the above processing, the validity of the mid-sagittal plane is determined in Step S1210 on the basis of whether an image of mid-sagittal plane can be created from the sagittal images reconstructed in Step S1208, and whether the mid-sagittal plane specified in Step S1207 is anatomically valid or not. When an image of mid-sagittal plane can be created, and the mid-sagittal plane is anatomically valid, the mid-sagittal plane is judged to be valid. Whether an image of mid-sagittal plane can be created or not is determined, for example, on the basis of the ratio of inclusion of the mid-sagittal plane specified in Step S1207 in the imaging regions of the five sagittal images obtained in Step S1208. That is, when the ratio obtained by calculation is not smaller than a predetermined ratio (for example, 75% or higher), it is determined that the creation is possible, and otherwise, it is determined that the creation is not possible. Further, whether the mid-sagittal plane is anatomically valid or not is determined on the basis of whether the position of the mid-sagittal plane locates at a position significantly deviated from the center of the head determined from the coronal image and the axial image (for example, the distance from the center of the head to the mid-sagittal plane is not smaller than ¼ of the width of the head calculated from the coronal image) or not. That is, when it locates at a significantly deviated position, it is judged to be invalid.

Figure 12A:
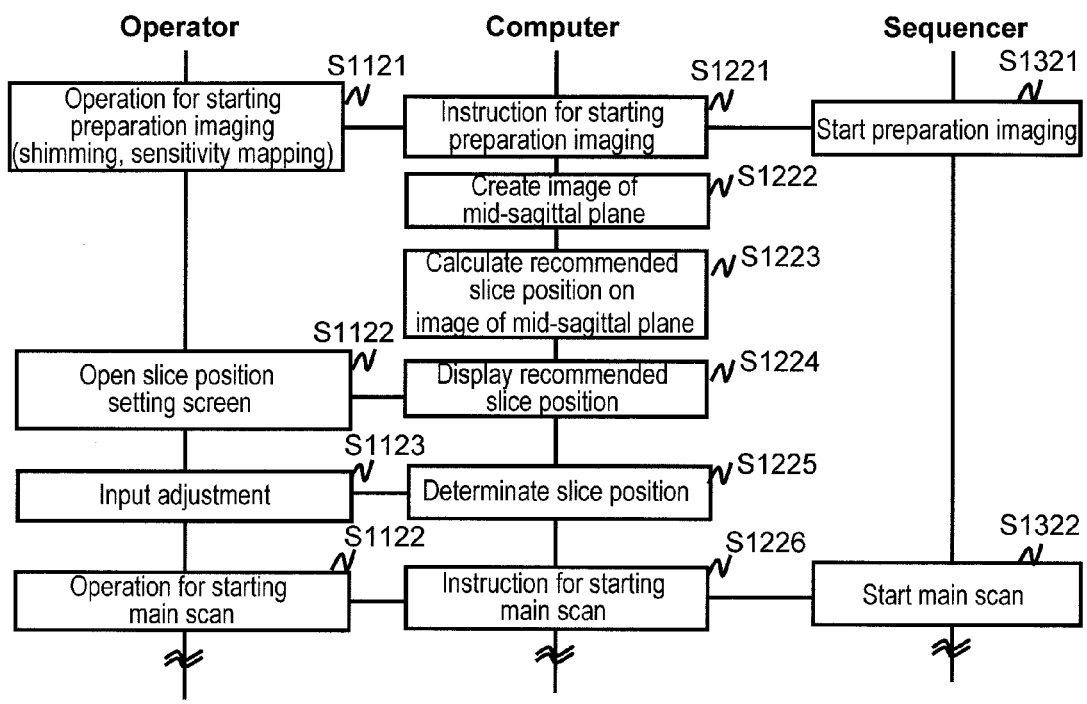
FIG. 12A is a chart for explaining measurement preparation processing according to the first embodiment.
Figure 12B:
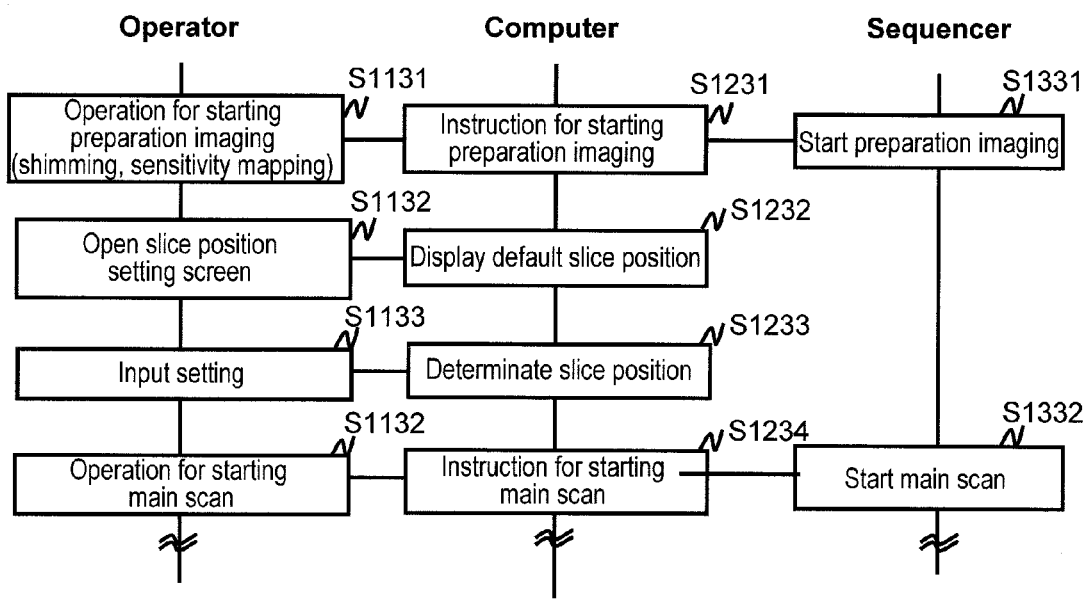
FIG. 12B is a chart for explaining measurement preparation processing according to the first embodiment.

Hereafter, processing for the case where the operator gives an instruction for continuing the measurement preparation processing, without retaking scout images, that is, directly after the scout scan, in Step S1103 will be explained with reference to FIG. 12A, and FIG. 12B. FIG. 12A shows a flow of the processing for such a case as mentioned above where it is further judged that the mid-sagittal plane is valid in Step S1210.

As shown in the chart, if an instruction for not retaking scout images is received in Step S1103, and it is judged that the mid-sagittal plane is valid in Step S1210, in the computer 110, the calculating part of recommended slice position 241 generates an image at the position of the mid-sagittal plane (image of mid-sagittal plane) from the sagittal image (Step S1222), and calculates a recommended slice position on the generated image (Step S1223). During the above processing, the operator gives an instruction for starting the preparation imaging (Step S1121). In the computer 110, the UI controlling part 210 receives the instruction from the operator, and the measurement controlling part 230 outputs an instruction to the sequencer 104 according to a pulse sequence and imaging parameters stored beforehand for the preparation imaging (Step S1221). The sequencer 104 operates the respective parts according to the instruction from the computer 110 to perform the preparation imaging (Step S1321). Although it is described in the chart that the computer 110 performs the processings of Steps S1222 and S1223 after the start of the preparation imaging, the computer 110 performs the processings of Steps S1222 and S1223 without waiting for the instruction of the operator for starting the preparation imaging.

When the operator performs an operation for opening a slice position setting screen for the main scan (Step S1122), in the computer 110, the UI controlling part 210 displays the information for specifying the recommended slice position calculated in Step S1223, for example, the region of recommended slice position based on the position, orientation, and imaging parameters set for the main scan (number of slices, thickness of slice, FOV etc.), scout images, and so forth on the display 110 (Step S1224). The operator inputs instructions for adjusting the displayed recommended slice position, if needed (Step S1123). In the computer 110, the UI controlling part 210 receives the input for the adjustment, and the determining part of slice position 240 adjusts the position of the slice position according to the received amount of adjustment to determine the final slice position for the main scan (Step S1225). In this case, the imaging parameters relating to the slice position for the main scan may be renewed according to the determined slice position. When an instruction for starting the main scan is received from the operator (Step S1124), in the computer 110, the measurement controlling part 230 sends a command to the sequencer according to a pulse sequence and imaging parameters stored beforehand for the main scan (Step S1226), and the sequencer 104 operates the respective parts according to the instruction from the computer 110 to perform the main scan (Step S1322).

When the input for the adjustment from the operator is received in Step S1225, in the computer 110, the determining part of slice position 240 may display the adjusted slice position on the display 111 as a recommended slice position, and then an instruction for adjustment may be received again. In such a configuration, an adjusted slice position is repeatedly displayed on the display 111 as a recommended slice position so that input for adjustment is possible, until an instruction for starting the main scan is received from the operator.

Hereafter, processing of the case where an instruction for not retaking the scout images is received in Step S1103, and the mid-sagittal plane is determined to be invalid in Step S1210 will be explained with reference to FIG. 12B. In the computer 110, the recommended slice position calculation processing is ended at that point. On the other hand, the operator gives an instruction for starting the preparation imaging (Step S1131). In the computer 110, the UI controlling part 210 receives the instruction from the operator, and the measurement controlling part 230 outputs a command to the sequencer 104 according to a pulse sequence and imaging parameters stored beforehand for the preparation imaging (Step S1231). The sequencer 104 operates the respective parts according to the instruction from the computer 110 to perform the preparation imaging (Step S1331).

When the operator performs an operation for opening the slice position setting screen for the main scan (Step S1132), in the computer 110, the UI controlling part 210 displays the scout images and a default slice position (such as transaxial slice position) determined on the basis of the set scan parameters (number of slices, thickness of slice, FOV etc.) as a recommended slice position on the display 110 (Step S1232). The operator adjusts the displayed default slice position on the scout images (Step S1133). In the computer 110, the UI controlling part 210 receives the input for the adjustment, and the determining part of slice position 240 determines the slice position according to the received input, and renews the imaging parameters relating to the slice position for the main scan according to the determined slice position (Step S1233). Also in this case, as in the case shown in FIG. 12A mentioned above, the input for the adjustment may be possible for any number of times. When the operator gives an instruction for starting the main scan (Step S1134), in the computer 110, the measurement controlling part 230 sends a command to the sequencer according to a pulse sequence and imaging parameters stored beforehand for the main scan (Step S1234), and the sequencer 104 operates the respective parts according to the instruction from the computer 110 to perform the main scan (Step S1332).

Figure 13A:
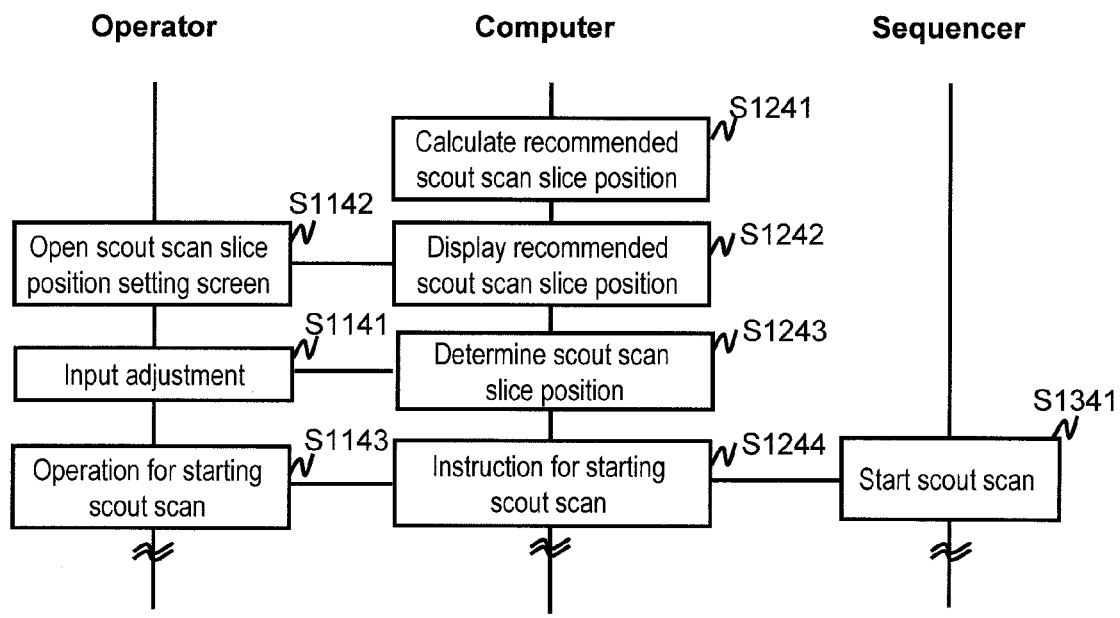
FIG. 13A is a chart for explaining measurement preparation processing according to the first embodiment.
Figure 13B:
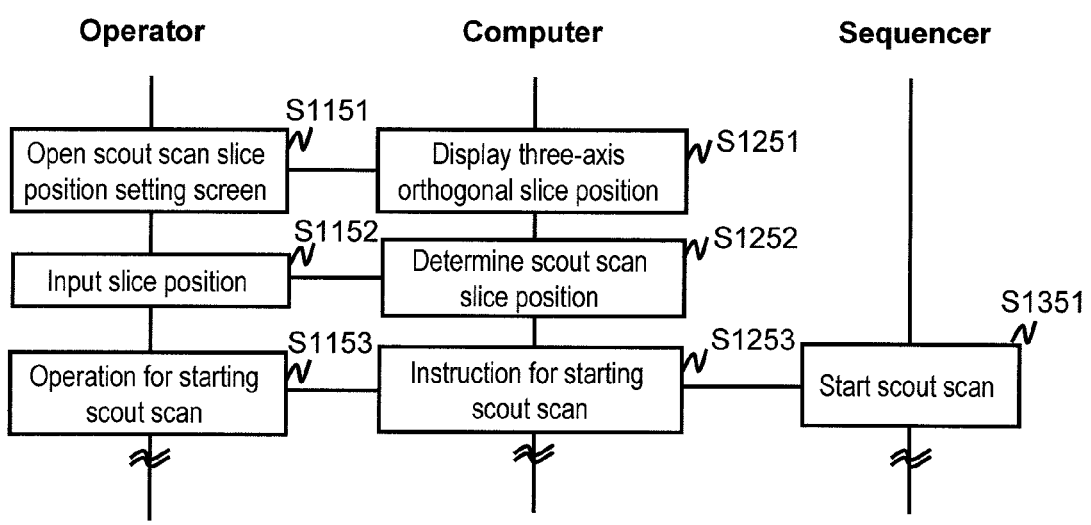
FIG. 13B is a chart for explaining measurement preparation processing according to the first embodiment.

Hereafter, processing of the case where an instruction for retaking the scout images is received in Step S1103 will be explained with reference to FIG. 13A and FIG. 13B. FIG. 13A is a chart for explaining the flow of the measurement preparation processing for such a case as mentioned above where it is further judged that the mid-sagittal plane is anatomically valid in the analysis of Step S1210. In such a case, in the computer 110, the calculating part of recommended slice position 241 calculates slices for scout scan for which the mid-sagittal plane specified in Step S1207 is obtainable as recommended slices for scout scan (Step S1241). And if the operator performs an operation for opening the scout scan slice setting screen (Step S1142), in the computer 110, the UI controlling part 210 receives a corresponding instruction, and displays scout images and the information for specifying the calculated recommended slice for scout scan on the display 111 (Step S1242). In the above operation, the operator does not necessarily need to perform the operation for opening the scout scan setting screen, and when an instruction for retaking is received, the display may be automatically switched to the scout scan setting screen to display the scout images and a recommended scout scan position. The operator inputs an instruction for adjusting the displayed recommended slice position for scout scan (Step S1141). In the computer 110, the UI controlling part 210 receives the input for the adjustment, and the determining part of slice position 240 adjusts the recommended slice for scout scan according to the received amount of adjustment to determine the final slice for scout scan (Step S1243). In this case, the imaging parameters relating to the slice position may be renewed according to the determined slice position. Also in this case, as in the case shown in FIG. 12A mentioned above, the input for the adjustment may be possible for any number of times. Thereafter, the processings of Steps S1101, S1201, S1301 and thereafter are repeated for each time.

Hereafter, the flow of the measurement preparation processing of the case where an instruction for retaking the scout images is received in Step S1103, and the mid-sagittal plane is further determined to be anatomically invalid in the analysis of Step S1210 will be explained with reference to FIG. 13B. In this case, if the operator performs an operation for opening the scout scan slice setting screen (Step S1151), in the computer 110, the UI controlling part 210 receives a corresponding instruction, and displays a three-axis orthogonal slice on the display 111 (Step S1251). The operator inputs an instruction for adjusting the displayed three-axis orthogonal slice for determining the slice for scout scan (Step S1152). In the computer 110, the UI controlling part 210 receives the input for the adjustment, and the determining part of slice position 240 determines the slice for scout scan according to the received amount of the adjustment (Step S1252). In this case, the imaging parameters relating to the slice position may be renewed according to the determined slice position. Also in this case, as in the case shown in FIG. 12A mentioned above, the input for the adjustment may be possible for any number of times. Thereafter, the processings of Steps S1101, S1201, S1301 and thereafter are repeated for each time.

The above is the flow of processing from the scout scan starting operation to the main scan starting operation in the case of routine examination of the head.

That is, in a routine examination of the head, the measurement controlling part 230 and the signal processing part 220 obtain a first image group consisting of one or more two-dimensional images parallel to a coronal plane, which is a first slice plane as one of mutually crossing two slice planes, and a second image group consisting of one or more two-dimensional images parallel to an axial plane, which is a second slice plane as the other of the mutually crossing two slice planes. Further, they obtain a fourth image group consisting of one or more two-dimensional images parallel to a sagittal plane, which is a fourth slice plane crossing both the first and second slice planes.

Further, the extracting means of anatomical feature 242 determines slope of the mid-sagittal line as a first anatomical feature from the first image group, and the mid-sagittal line from the second image group. And the determining part of slice plane 243 determines the mid-sagittal plane as a third slice plane from the slope of the mid-sagittal line and the mid-sagittal line determined by the extracting part of anatomical feature 242.

The calculating part of recommended slice position 241 generates a two-dimensional image of the mid-sagittal plane determined from the fourth image group as a third image. And by using the template model 800 constituted by a plurality of anatomical landmarks to be included in a recommended slice position, positions of these anatomical landmarks are specified on the third image, and a recommended slice position is determined on the basis of the positional relationship of the anatomical feature and recommended slice position registered beforehand in the information storing part for calculation of recommended slice position 330.

As explained above, according to this embodiment, image processing is executed in parallel with the scout scan to calculate a recommended slice position. Further, the scout scan to be executed is the same as that of the case where a slice position is manually set from scout images. Therefore, a recommended slice position can be presented to the operator without changing the flow of the conventional examination and without prolongation of the processing time due to addition of new processing. For this reason, operability of automatically obtaining a recommended slice position is not degraded.

Further, even when scout images are retaken, the retaking is performed after setting a more appropriate slice for scout scan as shown in FIG. 13A, and therefore scout images can be efficiently retaken. Furthermore, even if any recommended slice position or recommended slice for scout scan is not calculated as shown in FIG. 12B and FIG. 13B mentioned above, the processing time is not prolonged, and the same as that of the conventional procedure, and therefore examination efficiency is not degraded.

The aforementioned embodiment was explained by exemplifying the recommended slice position calculation processing for the case of setting an oblique plane significantly different from the three perpendicularly crossing slice planes, for which scout images are generally obtained, as the imaging plane, as in the case of examination of the head. Hereafter, however, the recommended slice position calculation processing for the case where the imaging plane substantially corresponds to any one of the three slice planes, for which scout images are obtained, will be explained with reference to a specific example. Also in this case, the recommended slice position calculation processing is executed by the calculating part of recommended slice position 241 by using algorithms, image processings, and anatomical features registered at the information storing part for calculation of recommended slice position 330. Hereafter, several types of examinations will be explained.

First, examination of the lumbar vertebra will be explained. In an examination of the lumbar vertebra, T1 emphasized image and T2 emphasized image of a sagittal plane (lumbar vertebra sagittal plane), and T1 emphasized image and T2 emphasized image of an intervertebral disc line are obtained. That is, the slice positions are two planes, the lumbar vertebra sagittal plane and the plane including the intervertebral disc line (intervertebral disc line plane). The lumbar vertebra examination sagittal plane is defined as a slice plane parallel to the spinal nerve, and the intervertebral disc line plane is defined as a plane having the same inclination of the intervertebral disc located under each of the first to fifth lumbar vertebrae. Therefore, the lumbar vertebra examination sagittal plane is determined by the position of lumbar vertebra and inclination of the spinal nerve. Further, the intervertebral disc line plane is determined by the position of intervertebral disc and inclination of the spinal nerve.

Therefore, at the information storing part of optimal scout scan 320, optimal scout scan information for examination of the lumbar vertebra is registered so that, for example, imaging is performed for a plurality of slices (for example, five slices) parallel to each of the coronal plane, the axial plane, and the sagittal plane in this order by using a pulse sequence of the GrE type for proton emphasis. Further, at the information storing part for calculation of recommended slice position 330, there are registered algorithms, image processings and anatomical features for, in the slice position processing, determining a lumbar vertebra position on an axial image, determining inclination of the spinal nerve on a coronal image, and determining a lumbar vertebra sagittal plane from these, and algorithms, image processings and anatomical features for determining a position of an intervertebral disc of the subject on a lumbar vertebra examination sagittal plane image, and determining an intervertebral disc line plane by using the previously determined inclination of the spinal nerve on the coronal image.

Hereafter, the details of the recommended slice position calculation processing performed in a lumbar vertebra examination by the calculating part of recommended slice position 241 will be explained.

First, on an axial image obtained at the beginning of the scout scan, the position of the lumbar vertebra, i.e., the position of the spinal nerve, is determined by calculation of the center of gravity of the image etc. Then, inclination of the spinal nerve is obtained by using the evaluation function of pixel values from a coronal image. And a plane passing the position of the spinal nerve obtained on the axial image and having the inclination of the spinal nerve obtained on the coronal image is defined as a recommended slice position of the lumbar vertebra sagittal plane. The processings mentioned above are completed before the main scan.

Then, an image of the lumbar vertebra examination sagittal plane is created by interpolation or the like from a sagittal image obtained by the scout scan. As the image of the lumbar vertebra examination sagittal plane, that obtained by the main scan may be used. And on the basis of edge emphasis on the lumbar vertebra examination sagittal plane image or the evaluation function of pixel values, the position of the intervertebral disc is specified. A plane passing the obtained position of the intervertebral disc, and perpendicular to the inclination of the spinal nerve is defined as a recommended slice position of the intervertebral disc line plane.

Hereafter, examination of the knee will be explained. In an examination of the knee, T2* emphasized image and T1 emphasized image of a coronal plane (knee coronal plane), T2* emphasized image and T1 emphasized image of a sagittal plane (knee sagittal plane), and T2 emphasized image of a diagnostic plane of the anterior cruciate ligament are obtained. That is, the slice positions are those of the three planes, the knee coronal plane, the knee sagittal plane, and the diagnostic plane of the anterior cruciate ligament.

At the information storing part of optimal scout scan 320, there is registered such optimal scout scan information for examination of the knee that imaging is performed for a plurality of slices (for example, five slices) for each of the axial plane, the sagittal plane and the coronal plane in this order by using a GrE type pulse sequence.

Hereafter, details of the recommended slice position calculation processing in examination of the knee performed by the calculating part of recommended slice position 241 according to algorithms and image processings registered at the information storing part for calculation of recommended slice position 330 as those for the knee are explained.

First, on an axial image obtained at the beginning of the scout scan, a line connecting the medial condyle of the femur and the lateral condyle of the femur is specified. Then, on a sagittal image, a line perpendicular to the tangential line of the articular surfaces of the femur and tibia is specified. And a plane parallel with the line connecting the medial condyle of the femur and the lateral condyle of the femur and perpendicular to the tangential line of the articular surfaces of the femur and tibia is defined to be a recommended slice position of the knee coronal plane. For determining the recommended slice position, the same procedure as that used for the midsagittal plane determination processing in the routine examination of the head or the like is used. The same shall apply to the examinations described hereinafter.

Then, a line perpendicular to the line connecting the medial condyle of the femur and the lateral condyle of the femur is specified from the axial image obtained by the scout scan. Further, an image of the knee coronal plane (knee coronal image) is created by interpolation or the like from the coronal image obtained by the scout scan. As the knee coronal image, that obtained by the main scan may be used. And a tangential line of the articular surfaces of the femur and tibia is specified on the knee coronal plane image. And a plane perpendicular to the tangential line of the articular surfaces of the femur and tibia and perpendicular to the line connecting the medial condyle of the femur and the lateral condyle of the femur is defined as a recommended slice position of a knee sagittal plane.

Then, an image of the knee sagittal plane (knee sagittal image) is created by interpolation or the like from the sagittal image obtained by the scout scan. As the knee sagittal image, that obtained by the main scan may be used. An image in which the anterior cruciate ligament is imaged is chosen from the knee sagittal images, and a line along the anterior cruciate ligament is specified on the knee sagittal image. Then, an image in which the anterior cruciate ligament is imaged is chosen from the knee coronal images, and a line along the anterior cruciate ligament is specified on the knee coronal image. And on the knee coronal image, a plane parallel to the anterior cruciate ligament and parallel to the anterior cruciate ligament is defined as a recommended slice position of the diagnostic plane of the anterior cruciate ligament.

Hereafter, examination of the shoulder will be explained. In an examination of the shoulder, T1 emphasized image and T2 emphasized image of a coronal plane (shoulder coronal plane), T1 emphasized image and T2 emphasized image of a sagittal plane (shoulder sagittal plane), and T1 emphasized image and T2 emphasized image of an axial plane (shoulder axial plane) are obtained. That is, the slice positions are those of these three planes, the shoulder coronal plane, the shoulder sagittal plane, and the shoulder axial plane.

At the information storing part of optimal scout scan 320, there is registered such optimal scout scan information for examination of the shoulder that imaging is performed for a plurality of slices (for example, five slices) for each of the axial plane, the sagittal plane and the coronal plane in this order by using a GrE type pulse sequence.

Hereafter, details of the recommended slice position calculation processing in examination of the shoulder performed by the calculating part of recommended slice position 241 according to algorithms and image processings registered at the information storing part for calculation of recommended slice position 330 as those for the shoulder will be explained.

First, from axial images obtained at the beginning of the scout scan, an image in which the supraspinous muscle is imaged is chosen, and a line parallel to the supraspinous muscle is specified on that image. Then, a line along the humerus is specified on a sagittal image obtained by the scout scan. And a plane parallel to the supraspinous muscle and parallel to the humerus is defined as a recommended slice position of the shoulder coronal plane.

Then, an image in which the caput of bone and the scapula are imaged is chosen from the axial images obtained by the scout scan, and a line perpendicular to the tangential line of the articular surfaces is specified on that image. Further, an image of the shoulder coronal plane (shoulder coronal image) is created by interpolation or the like from a coronal image obtained by the scout scan. As the shoulder coronal image, one obtained by the main scan may be used. And a line perpendicular to the line connecting the caput of bone and the scapula is specified on the shoulder coronal image. And a plane perpendicular to the line connecting the caput of bone and the scapula, and perpendicular to the tangential line of the articular surfaces of the caput of bone and the scapula is defined as a recommended slice position of the shoulder sagittal plane.

Then, an image of the shoulder sagittal plane (shoulder sagittal image) is created by interpolation or the like from a sagittal image obtained by the scout scan. As the shoulder sagittal image, one obtained by the main scan may be used. And a straight line perpendicular to the line along the humerus is specified on the shoulder sagittal image. Then, a straight line connecting the acromion and the clavicle is specified on the shoulder coronal image. And a plane perpendicular to the humerus, parallel to the straight line connecting the acromion and the clavicle, and parallel to the tangential line of the articular surfaces is defined as a recommended slice position of the shoulder axial plane.

The flow of the whole examination in which the recommended slice position calculation processing of each region explained above is incorporated is the same as that of the routine examination of the head described above. As for those examination regions, the plane corresponding to the midsagittal plane is the lumbar vertebra sagittal plane in the case of the lumbar vertebra, the knee coronal plane in the case of the knee, or the shoulder coronal plane in the case of the shoulder. Therefore, in Step S1210, validity of each of these planes is analyzed and judged.

That is, in the case of examination of the lumbar vertebra, the measurement controlling part 230 and the signal processing part 220 use a first slice plane as the axial plane, a second slice plane as the coronal plane, and a fourth slice plane as the sagittal plane to obtain groups of two-dimensional images consisting of one or more images parallel to one of the planes as a first image group, a second image group, and a fourth image group, respectively. And the extracting part of anatomical feature 242 extracts position of the spinal nerve on the axial image as a first anatomical feature, and inclination of the spinal nerve on the coronal image as a second anatomical feature. The determining part of slice plane 243 determines a plane passing the position of the spinal nerve and having the inclination of the spinal nerve as a lumbar vertebra sagittal plane, i.e., as a third slice plane. The calculating part of recommended slice position 241 creates images of the third slice plane by interpolation, which images constitute the third image group. The extracting part of anatomical feature 242 extracts position of the intervertebral disc on a lumbar vertebra sagittal plane as a third anatomical feature. And the determining part of slice plane 243 determines a fifth slice plane from the first anatomical feature, or the first anatomical feature and the third anatomical feature, and the calculating part of recommended slice position 241 defines the fifth slice plane as a recommended slice position.

Further, in the case of examination of the knee, the measurement controlling part 230 and the signal processing part 220 use a first slice plane as the axial plane, a second slice plane as the sagittal plane, and a fourth slice plane as the coronal plane to obtain groups of two-dimensional images consisting of one or more images parallel to one of the planes as a first image group, a second image group, and a fourth image group, respectively. And the extracting part of anatomical feature 242 extracts a line connecting the medial condyle of the femur and the lateral condyle of the femur as a first anatomical feature, a line perpendicular to the tangential line of the articular surfaces of the femur and tibia on the sagittal image as a second anatomical feature, and a line perpendicular to the line connecting the medial condyle of the femur and the lateral condyle of the femur on the axial image as a fourth anatomical feature. The determining part of slice plane 243 determines the knee coronal plane specified on the basis of the first anatomical feature and the second anatomical feature as a third slice plane. The calculating part of recommended slice position 241 creates a third image by interpolation or the like as an image of the third slice plane. And the extracting part of anatomical feature 242 specifies a tangential line of the articular surfaces of the femur and tibia on the third image as a third anatomical feature.

Furthermore, the determining part of slice plane 243 determines the knee sagittal plane specified on the basis of the third anatomical feature and the fourth anatomical feature as a fifth slice plane, and the calculating part of recommended slice position 241 creates an image of the fifth slice plane by interpolation or the like as a fifth image. The extracting part of anatomical feature 242 extracts a line along the anterior cruciate ligament on the knee sagittal image as a fifth anatomical feature, and extracts a line along the anterior cruciate ligament on the knee coronal image as a sixth anatomical feature. The determining part of slice plane 243 determines a plane parallel to the fifth anatomical feature and parallel to the sixth anatomical feature as a sixth slice plane, and the calculating part of recommended slice position 241 defines the sixth slice plane as a recommended slice position.

In the case of examination of the shoulder, the measurement controlling part 230 and the signal processing part 220 use a first slice plane as the axial plane, a second slice plane as the sagittal plane, and a fourth slice plane as the coronal plane to obtain groups of two-dimensional images consisting of one or more images parallel to one of the planes as a first image group, a second image group, and a fourth image group, respectively. And the extracting part of anatomical feature 242 extracts a line parallel to the supraspinous muscle on the axial image as a first anatomical feature, a line along the humerus on the sagittal image as a second anatomical feature, and a line perpendicular to the tangential line of the articular surfaces on the axial image as a fourth anatomical feature. The determining part of slice plane 243 determines the shoulder coronal plane specified on the basis of the first anatomical feature and the second anatomical feature as a third slice plane. The calculating part of recommended slice position 241 creates a third image by interpolation or the like as an image of the third slice plane. And the extracting part of anatomical feature 242 specifies a line perpendicular to the line connecting the caput of bone and the scapula on the third image as a third anatomical feature.

Furthermore, the determining part of slice plane 243 determines the shoulder sagittal plane specified on the basis of the third anatomical feature and the fourth anatomical feature as a fifth slice plane, and the calculating part of recommended slice position 241 creates an image of the fifth slice plane by interpolation or the like as a fifth image. The extracting part of anatomical feature 242 extracts a straight line perpendicular to the line along the humerus on the shoulder sagittal image as a fifth anatomical feature, and extracts a straight line connecting the acromion and the clavicle on the shoulder coronal image as a sixth anatomical feature. The determining part of slice plane 243 determines a plane parallel to the fifth anatomical feature and parallel to the sixth anatomical feature as a sixth slice plane, and the calculating part of recommended slice position 241 defines the sixth slice plane as a recommended slice position.

The routine examination of the head according to this embodiment was explained by exemplifying a case where the scout images are obtained with a pulse sequence for obtaining T1 emphasized images in which clear contrast of tissues in the head is obtained. However, the pulse sequence to be used is not limited to such a pulse sequence. For example, a pulse sequence for obtaining T2 emphasized images may also be used. However, in such a case, the pattern of pixel values of the image differs from that obtained in this embodiment, and therefore it is necessary to adjust the evaluation function for the image processing.

Further, this embodiment was explained by exemplifying a case where the recommended slice position calculation processing is performed by the calculating part of recommended slice position 241 in parallel with the scout scan. However, this embodiment is not limited to such a configuration. For example, the recommended slice position calculation processing may be performed after the entire scout scan is completed.

Further, for every slice plane, the recommended slice position calculation processing may be performed for the image of that slice plane before imaging for the next slice plane, and the result may be reflected in the imaging for the next slice plane. In such a case, for example, a function of recognizing the body position of the subject 103, and adjusting the position for the measurement of the next plane is provided. In the case of the routine examination of the head, for example, after the measurement for the coronal plane, on the basis of the obtained reconstituted image, the slice position of the z-axis direction for the axial imaging is adjusted so that the axial image should be within the aforementioned range, and measurement is performed for the axial plane. Furthermore, measurement for the sagittal plane is performed after the slice position is adjusted so that the position of the mid-sagittal plane calculated from the coronal image and the axial image should be included. With such a configuration, even if the head is set with a certain inclination, it does not become necessary to retake the scout images.

Furthermore, magnetic resonance signals zero phase-encoded for the x-axis, y-axis, and z-axis may be obtained before the scout scan to specify approximate position and size of the subject 103, and then the position for the scout scan may be determined.

Further, this embodiment was explained by exemplifying a case where the operator is required to select whether the imaging is continued or the scout scan is performed again, after the entire scout scan is completed. However, this embodiment is not limited to such a configuration. The calculating part of recommended slice position 241 may not have a configuration for receiving such selection, and it may advance the processing without the selection to calculate a recommended slice position, and in the case of routine examination of the head, for example, if the analysis result of the mid-sagittal plane is not valid, a message indicating that accuracy is not reliable may be displayed together with a recommended slice position. Alternatively, the processing may be advanced when the processing analysis result of the mid-sagittal plane is valid, and a message for recommending to perform the scout scan again may be displayed on the display 111, and the processing may be ended, when the processing analysis result is invalid. Furthermore, when the processing analysis result of the mid-sagittal plane is invalid, the calculating part of recommended slice position 241 may calculate a position at which the mid-sagittal plane can be created, and the scout scan may be automatically performed again at that position. Furthermore, when the calculating part of recommended slice position 241 judges that the mid-sagittal plane significantly inclines at the time of the analysis of the position of the mid-sagittal plane, a message for recommending that the scout scan be performed again may be displayed at that point. According to these configurations, the operator can judge appropriateness of the scout images without confirming the images, and therefore examination efficiency is improved.

Further, this embodiment was explained by exemplifying a case where the operator performs an operation for opening a slice position setting screen before the main scan, and input for adjustment by the operator is received on the displayed recommended slice position. However, this embodiment is not limited to such a configuration. When a recommended slice position is valid, the determining part of slice position 240 may automatically determine the recommended slice position as a slice position, and the main scan may be performed. For example, in the case of routine examination of the head, when the mid-sagittal plane is analyzed to be valid, an instruction for starting the main scan is waited without displaying a screen for receiving input for setting for determining the position. Only when it is analyzed to be invalid, before receiving an instruction for starting the main scan, a screen for receiving input for setting for determining the position is displayed, or a message indicating that the accuracy is poor, or recommending that the scout scan be performed again is displayed. Furthermore, use or no use of the function of receiving input for the adjustment on the recommended slice position may be selectable. With such a configuration, when the calculated mid-sagittal plane is valid, the operations to be performed by the operator and the processing time of the whole examination are decreased.

Further, this embodiment was explained by exemplifying a case where the processings up to the calculation of a recommended slice position are automatically performed. However, this embodiment is not limited to such a configuration. For example, setting of the slice position may be performed by the operator. In such a case, in the case of routine examination of the head, for example, the calculating part of recommended slice position 241 executes the processings up to the creation of an image of mid-sagittal plane. And when the operator performs an operation for opening the screen for setting for determining position before the main scan, the determining part of slice position 240 displays an image of mid-sagittal plane, and receives input of the operator. The operator sets a slice position on the image of mid-sagittal plane calculated by the calculating part of recommended slice position 241. In such a configuration, together with the calculated image of mid-sagittal plane, the obtained scout images (coronal image, axial image, sagittal image) may also be displayed on the display 111. With such a configuration, the operation for manually setting the slice position is made easier for the operator. Further, when the head is set with inclination, the image of mid-sagittal plane, conventionally obtained as a plurality of images, can be confirmed in one image, and thus operation for determining the position becomes easier.

Further, this embodiment was explained by exemplifying a case where a list of slice positions is contained beforehand in the information storing part for calculation of recommended slice position 330. However, this embodiment is not limited to such a configuration. There may be provided such a function that the operator can add a new item of the list of slice positions. For example, the operator sets a slice position through the display 111 and the input device 116 on an image in which the position of the anatomical feature serving as a mark is already specified. And the relation of them is registered at the list of slice positions with an arbitrary item name. For the setting, scout images obtained in the past, scout images obtained for the patient of interest, scout images of standard human and so forth are used. With using any of these images, an anatomical feature is manually extracted, or automatically extracted by an image processing. As an interface to be used, an interface for exclusive use may be provided, or the interface for determining the slice position may be used. In this case, a function of saving the inputted information in the list of slice positions is added. Further, slice positions set in examinations conducted in the past may be saved in the list of slice positions.

Further, the list of slice positions may be registered by the operator at every examination. First, at the time of setting imaging parameters of the pulse sequence for the main scan, a slice position is displayed as a transaxial slice on the basis of the set parameters (number of slices, thickness of slice, FOV etc.). At this time, a scout image in which position of an anatomical feature is already specified is displayed together. This image may be a scout image obtained by imaging performed in the past etc., or a scout image of a standard human. Then, the operator manually sets a slice position using the anatomical feature of the image displayed together as a mark. At this time, the computer 110 defines the manually set position as the slice position for the main scan, and saves the positional relationship with the position of the anatomical feature to be automatically recognized. In the above operation, the operator can set the position of the slice position with feeling similar to that of the conventional examination, and therefore the operator is not bothered with advance preparations. Further, any special user interface is not required. Furthermore, change of the protocol, including setting of the position of the slice position, during the examination becomes possible.

Second Embodiment

Hereafter, the second embodiment of the present invention will be explained. The MRI apparatus according to this embodiment has basically the same configurations as those of the first embodiment. However, in this embodiment, there is provided a function of memorizing amount of adjustment received from the operator as learning data after a recommended slice position or a recommended slice for scout scan is displayed, and reflecting it in the subsequent processings. Hereafter, explanation will be made with focusing on the configurations different from those of the first embodiment.

Figure 14:
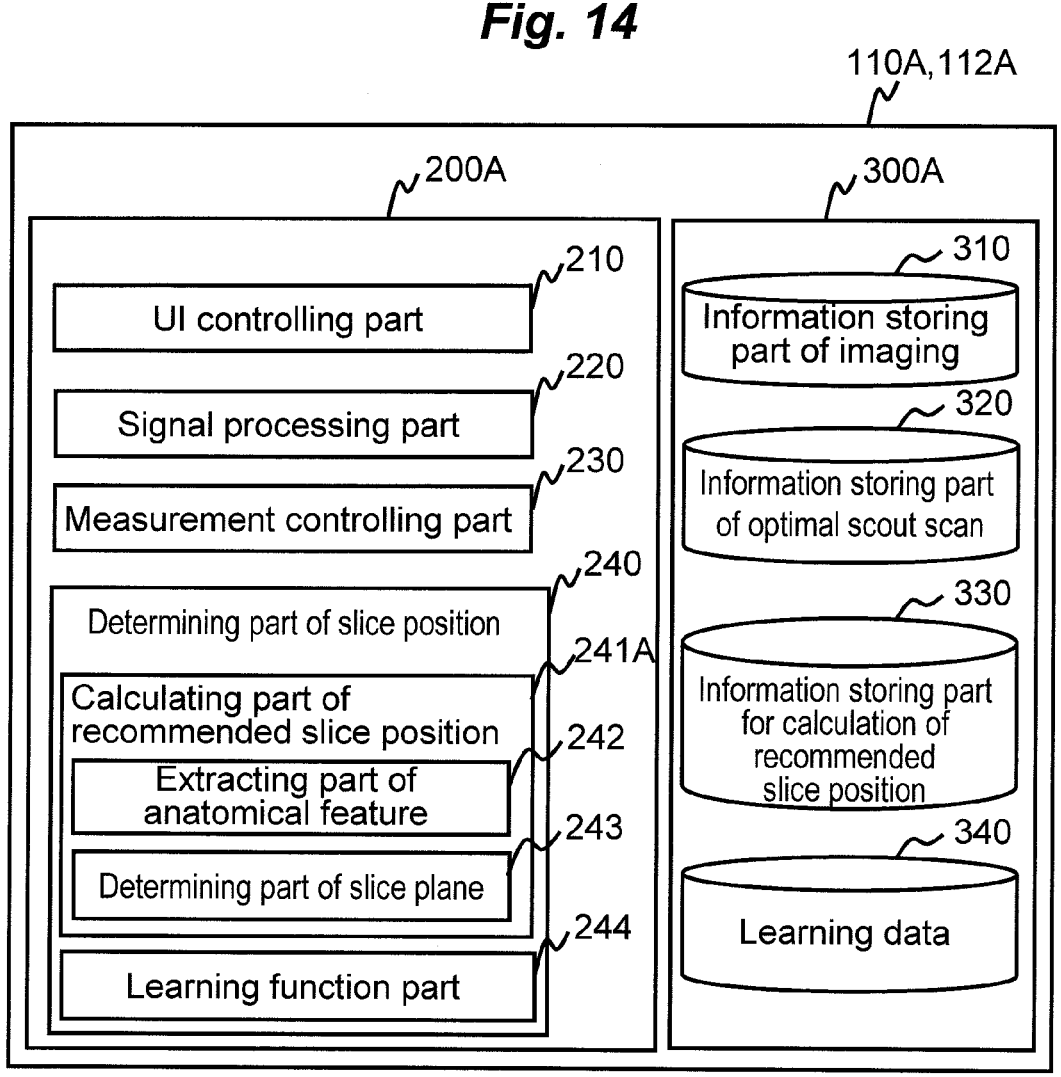
FIG. 14 is a functional block diagram of a computer according to the second embodiment.

FIG. 14 is a functional block diagram of an information processor constituted by a computer 110A and a storage device 112A according to this embodiment. In the information processor according to this embodiment, in addition to the same configurations as those of the first embodiment, the determining part of slice position 240 of a control part 200A is provided with a learning function part 244, and a storing part 300B is provided with a learning data storing part 340, respectively. Further, a calculating part of recommended slice position 241A is provided instead of the calculating part of recommended slice position 241.

Also in this embodiment, the computer 110A is equipped with CPU and a memory, and the functions of the control part 200A implemented by the computer 110A are realized by CPU by loading programs stored in the storage device 112A to the memory and executing them. Further, the storing part 300A is realized on the storage device 112A. All or a part of the functions may be realized by an information processor as a general-purpose information processor that is independently provided from the MRI apparatus 100, and can transmit and receive data to or from the MRI apparatus 100. Similarly, a part or all of the storing part 300A may be realized by an external storage device that is independently provided from the MRI apparatus 100, and can transmit and receive data to or from the MRI apparatus 100.

The learning function part 244 extracts amounts of adjustments added by the operator to the recommended slice position and recommended scout slice calculated by the calculating part of recommended slice position 241A in step S1225 and S1243 mentioned above, and store them in the learning data storing part 340 as learning data. The learning data are registered as those corresponding to each objective imaging region.

The learning data registered at the learning data storing part 240 consist of adjustment amounts of angle and position added by the operator to the recommended slice position. The learning function part 244 collects adjustment amounts whenever adjustment is made, and it renews the learning data registered at the learning data storing part 340 as those corresponding to each objective imaging region to be the newest.

In addition, as the learning data, average of changing amounts (amounts of adjustment) added over a plurality of times of examinations may be registered. Further, such an average calculated only with values appearing with high frequency in amounts of adjustment collected in a plurality of times of examination may be registered. By registering an average calculated only with values appearing with high frequency, learning of an amount of positional adjustment in an examination where exceptional positional adjustment is performed can be avoided. Precision of the correction values as those for usual examination can be thereby enhanced. Furthermore, a threshold value of the amount of adjustment may be provided, and an average calculated only with values not exceeding the threshold value may be registered. Further, learning data may be clustered with age, sex of subjects, size of examination region, direction of setting, characteristic degree of anatomical feature, etc., and an average of adjustment values may be calculated within the same cluster, and registered. With such a configuration, for example, correction values corresponding to individual differences can be obtained as learning data.

The calculating part of recommended slice position 241A uses the registered learning data as correction values for the next calculation. That is, in the aforementioned examination preparation processing, it calculates a recommended slice position and a recommendation slice for scout scan in Steps S1223 and S1241, respectively, then refers to the learning data storing part 340, when learning data are registered for the objective imaging region, corrects the calculation result by using the corresponding learning data, and defines the corrected slices as a recommended slice position and a recommendation slice for scout scan, respectively.

As explained above, according to this embodiment, in addition to the same effects as those of the first embodiment, a recommended slice position can be obtained with still higher accuracy. For example, when the slice position to be set differs for every facility or every operator, a slice position corresponding to each can be automatically outputted.

In addition, an interface, allowing the operator to choose whether the amount of adjustment should be learned or not, may be provided. The learning function part 244 performs the aforementioned processing, only when the operator chooses to use the adjustment learning function. Furthermore, whether the learning data are reflected in the recommended slice position and the recommended slice for scout scan or not may be selectable for the operator. The calculating part of recommended slice position 241 performs the aforementioned processing, only when the operator chooses to allow reflection of the learning data. The selection may be performable for every measurement, every imaging, or every examination.

Further, not only amounts of adjustments added to a recommended slice position or a recommended slice for scout scan, but also, in the case of routine examination of the head, for example, shape of final template model, initial disposition of template model, objective subject, and so forth may be stored as the learning data.

Furthermore, when the main scan using the same pulse sequence and imaging parameters is performed in another examination defined by a different protocol, whether learning data as operation tendency of an operator is shared or not may be selectable. With such a configuration, when the same imaging is performed with different protocols, the learning function can be used according to the preference of the operator.

Further, the learning function part 244 can also be used for setting a position of a recommended slice position. As explained for the first embodiment mentioned above, change added by the operator to the slice position displayed as a transaxial slice as the initial setting is stored, and it is reflected to the processings of the next time and thereafter. This configuration provides an advantage that the operator does not need to set a position of a recommended slice position beforehand.

Third Embodiment

Hereafter, the third embodiment of the present invention will be explained. The MRI apparatus according to this embodiment has basically the same configurations as those of either one of the aforementioned embodiments. However, in this embodiment, the calculating part of recommended slice position used in the first embodiment and the second embodiment is used for MPR processing. Hereafter, this embodiment will be explained with focusing on the configurations different from those of the embodiments described above.

Figure 15:
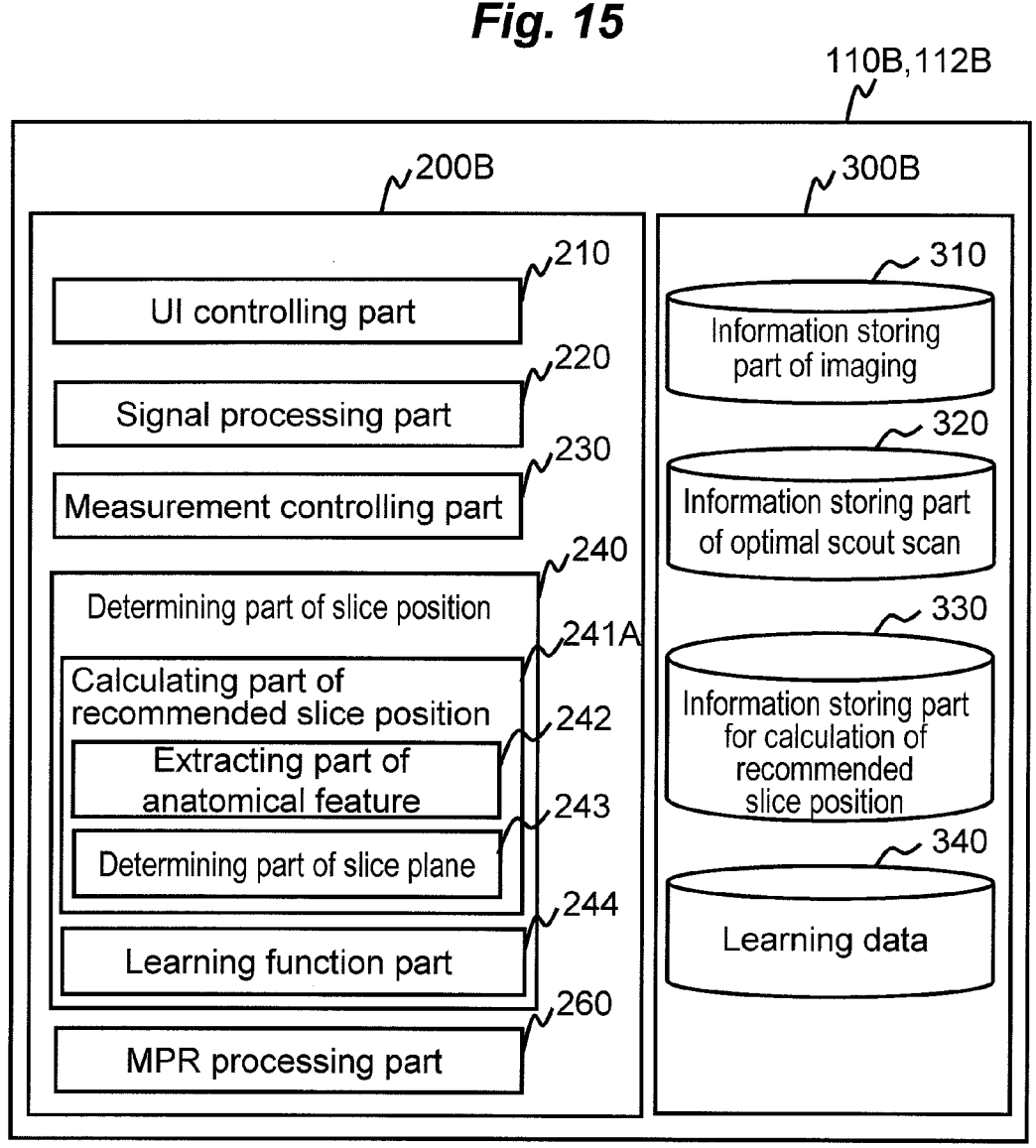
FIG. 15 is a functional block diagram of a computer according to the third embodiment.

FIG. 15 is a functional block diagram of an information processor constituted by a computer 110B and a storage device 112B according to this embodiment. The information processor according to this embodiment is basically the same as that of either one of the information processors of the aforementioned embodiments, but in the information processor of this embodiment, in addition to the same configurations as those of the aforementioned embodiments, the control part 200B is provided with an MPR processing part 260. The learning function part 244 and the learning data 340 may not be provided.

The MPR processing part 260 generates an interface screen for the MPR processing (MPRIF screen), and displays it on the display 111 through the UI controlling part 210. The MPRIF screen is provided with a region for displaying the obtained three-dimensional data, and an instruction-receiving region for receiving input by the operator. This region receives information for specifying a slice desired to be diagnosed slice (extracting slice) and parameters for specifying the extracting slice (slice parameters), such as FOV, number of slices, thickness of slice and interval of slices, from the operator.

The information for specifying the extracting slice is, in the case of the head, for example, information on a plane parallel to the OM line, a plane parallel to the AP-AC line, etc. Further, setting of the slice parameters may be attained with any type of procedure, such as selection from a list, and manual setting by the operator on an image displayed on the display region. In the case of selecting them from a list, a visual support using a graphical interface may be provided. Further, an extracting slice extracted in the past may be displayed, and an interface for simply receiving an instruction for whether the operator consent to use it or not may be provided. In this case, only when an instruction for not consenting to use it is received, the screen changes to a screen for receiving setting of slice parameters. With this configuration, the same slice as an extracting slice set in the past can be easily specified.

When an instruction for starting the MPR processing is received from the operator, the MPR processing part 260 first creates images for at least two mutually crossing planes from the three-dimensional data. For example, in the case of the head, an image parallel to the coronal plane, an image parallel to the axial plane, and an image parallel to the sagittal plane are created. The calculating part of recommended slice position 241 performs the same processings as those of the aforementioned embodiments in the same manner for each of the created images to calculate an extracting slice as a recommended slice position. And the MPR processing part 260 generates an image of the calculated extracting slice from the three-dimensional data, and the UI controlling part 210 displays the generated image on the display.

In this embodiment, in the case of the head, for example, when the position of the mid-sagittal plane is judged to be an anatomically invalid position, an error message is displayed. In this case, for example, a three-axis orthogonal slice is displayed without calculating an extracting slice, and the operator manually sets an extracting slice.

Further, also in this embodiment, information on algorithms for the processings, type of image processing, positional relationship of extracting slice and an anatomical feature, and so forth is stored beforehand in the information storing part for calculation of recommended slice position 330.

Further, the MPR processing part 260 may produce images for the slices in the same order as that of the scout scan stored in the information storing part of optimal scout scan 320, and after generation of required images is completed, the calculating part of recommended slice position 241 may perform the recommended slice position creation processing in parallel with the image generation processing performed by the MPR processing part 260.

As explained above, according to this embodiment, a desired diagnosis image is easily produced from three-dimensional data in a short time.

As explained above, according to the aforementioned embodiments, at the time of setting a slice position, image processing is performed simultaneously with the same two-dimensional scout scan as that of the case of manually setting the slice position to calculate a recommended slice position and present it, and therefore the operability for determining the position of the slice position can be improved without changing the flow of the conventional examination and without generating prolongation of the time required for the recommended slice position calculation processing. Furthermore, the processing for calculating a recommended slice position can also be applied to the processing for automatically calculating an extracting slice in MPR, and the examination efficiency in the post-processing is also improved.

Although the embodiments described above were explained with reference to examples in which the present invention was applied to an MRI apparatus, the apparatus to which the present invention is applied is not limited to an MRI apparatus. The calculating part of recommended slice position used in the aforementioned embodiments can be used for calculation of recommended slice position in various kinds of medical imaging apparatuses and imaging apparatuses in which an arbitrary plane in a three-dimensional space can be set as a slice position.

Description of Numerical Notations

100: MRI Apparatus, 101: magnet, 102: gradient magnetic field coil, 103: subject (living body), 104: sequencer, 105: gradient magnetic field power supply, 106: radio frequency magnetic field generator, 107: RF coil, 108: RF probe, 109: receiver, 110: computer, 111: display, 112: storage device, 113: shim coil, 114: shim power supply, 115: bed (table), 116: input device, 200: control part, 200A: control part, 200B: control part, 210: UI controlling part, 220: signal processing part, 230: measurement controlling part, 240: determining part of slice position, 241: calculating part of recommended slice position, 241A: calculating part of recommended slice position, 242: extracting part of anatomical feature, 243: determining part of slice plane, 244: learning function part, 260: MPR processing part, 300: storage part, 300A: storage part, 301: coronal image, 302: axial image, 303: sagittal image, 304: axis of coordinates, 310: information storing part of imaging, 320: information storing part of optimal scout scan, 330: information storing part for calculation of recommended slice position, 340: learning data storing part, 501: added image, 502: head region, 503: background region, 504: plot, 505: slope of linear function, 511: one-dimensional projection image on x-axis, 512: width of head, 513: threshold value, 521: one-dimensional projection image on z-axis, 522: differential value of reciprocal, 531: vertex, 532: point, 533: range, 534: slice position, 601: gradation corrected image, 602: added image, 603: center of gravity, 604: one-dimensional projection image on x-axis, 605: width of head, 606: angle, 607: ½ of width, 608: minimum, 609: plot, 610: inclination α, 611: mid-sagittal plane passing point P, 612: mid-sagittal line, 621: region of anterior wall side, 622: region of posterior wall side, 800: template model, 701: intersection line, 801: landmark, 810: image of mid-sagittal plane, 820: standard model, 901: image of mid-sagittal plane, 902: center of gravity, 903: one-dimensional projection image on z-axis, 904: length of head, 905: contour coordinates, 906: linear function, 907: intersection with altitude, 908: contour coordinate, 910: linear function, 911: slope of linear function, 913: width of head, 920: initial position, 1002: OM line, 1003: region of whole brain, 1004: orientation of recommended slice position, 1005: region of recommended slice position

The invention claimed is:

1. A medical imaging apparatus enabling imaging of an arbitrary slice in a three-dimensional space, which comprises:

at least one hardware processor and memory configured to effect:
an image acquirer configured to acquire a first image group consisting of one or more two-dimensional images parallel to a first slice plane, which is one of mutually crossing two slice planes, and a second image group consisting of one or more two-dimensional images parallel to a second slice plane, which is the other of the mutually crossing two slice planes,
an anatomical feature extractor configured to extract information on an anatomical feature defined beforehand from a two-dimensional image,
a recommended slice position calculator configured to calculate a recommended slice position to be recommended as a slice position, and
a recommended slice position calculation storer configured to store recommended slice position calculation information necessary for calculating the recommended slice position according to an imaging region, wherein:
the anatomical feature extractor is configured to extract information on a first anatomical feature from the first image group, and extract information on a second anatomical feature from the second image group, and
the recommended slice position calculator is configured to calculate the recommended slice position by using the information on the first anatomical feature and the information on the second anatomical feature according to the recommended slice position calculation information.

2. The medical imaging apparatus according to claim 1, wherein:
the recommended slice position calculator further comprises:
a slice plane determiner configured to determine a slice plane,
an image generator configured to generate a two-dimensional image of a slice plane determined by the slice plane determiner from a reconstructed image, and a anatomical landmarks determiner configured to specify a position of an anatomical landmark on an image,
the slice plane determiner is further configured to determine a third slice plane using the first anatomical feature and the second anatomical feature according to the recommended slice position calculation information,
the image acquirer is further configured to acquire a fourth image group consisting of one or more two-dimensional images parallel to a fourth slice plane crossing both the first slice plane and the second slice plane,
the image generator is further configured to generate a two-dimensional image of the third slice plane as a third image from the fourth image group,
the anatomical landmarks determiner is further configured to specify positions of a plurality of anatomical landmarks to be included in the recommended slice position on the third image according to the recommended slice position calculation information, and
the recommended slice position calculator is further configured to define a slice plane crossing the third slice plane and including a plurality of the anatomical landmarks as the recommended slice position.

3. The medical imaging apparatus according to claim 2, wherein:
the recommended slice position calculation storer is further configured to store a template model constituted by a plurality of coordinate points corresponding to a plurality of anatomical landmarks to be included in the slice position, and
the anatomical landmarks determiner is further configured to perform fitting with the template model to specify positions of a plurality of the anatomical landmarks on the third image.

4. The medical imaging apparatus according to claim 1, wherein:
the recommended slice position calculator further comprises a slice plane determiner configured to determine a slice plane,
the slice plane determiner is further configured to determine a third slice plane using the first anatomical feature and the second anatomical feature according to the recommended slice position calculation information, and
the recommended slice position calculator is further configured to define the third slice plane as the recommended slice position.

5. The medical imaging apparatus according to claim 4, wherein:
the recommended slice position calculator further comprises an image generator configured to generate a two-dimensional image of a slice plane determined by the slice plane determiner from a reconstructed image,
the image acquirer is further configured to acquire a fourth image group consisting of one or more two-dimensional images parallel to a fourth slice plane crossing both the first slice plane and the second slice plane,
the image generator is further configured to generate a two-dimensional image of the third slice plane as a third image from the fourth image group,
the anatomical feature extractor is further configured to extract information on a third anatomical feature from the third image according to the recommended slice position calculation information,
the slice plane determiner is further configured to determine a fifth slice plane using either one of the information on the first anatomical feature and the information on the second anatomical feature, and the information on the third anatomical feature according to the recommended slice position calculation information, and
the recommended slice position calculator is further configured to define the fifth slice plane as a second recommended slice position.

6. The medical imaging apparatus according to claim 4, wherein:
the recommended slice position calculator further comprises an image generator configured to generate a two-dimensional image of a slice plane determined by the slice plane determiner from a reconstructed image,
the image acquirer is further configured to acquire a fourth image group consisting of one or more two-dimensional images parallel to a fourth slice plane crossing both the first slice plane and the second slice plane,
the image generator is further configured to generate a two-dimensional image of the third slice plane as a third image from the fourth image group,
the anatomical feature extractor is further configured to extract information on a third anatomical feature from the third image, and extract information on a fourth anatomical feature from the first image group according to the recommended slice position calculation information,
the slice plane determiner is further configured to determine a fifth slice plane using the information on the third anatomical feature and the information on the fourth anatomical feature according to the recommended slice position calculation information, and the recommended slice position calculator is further configured to define the fifth slice plane as a second recommended slice position.

7. The medical imaging apparatus according to claim 6, wherein:

the image generator is further configured to generate a two-dimensional image of the fifth slice plane as a fifth image from the second image group, the anatomical feature extractor is configured to extract information on a fifth anatomical feature from the fifth image, and extract information on a sixth anatomical feature from the third image according to the recommended slice position calculation information, the slice plane determiner is configured to determine a sixth slice plane using the information on the fifth anatomical feature, and the information on the sixth anatomical feature according to the recommended slice position calculation information, and the recommended slice position calculator is configured to define the sixth slice plane as a third recommended slice position.

8. The medical imaging apparatus according to claim 4, which further comprises:

a scout scan controller configured to control acquisition of the two-dimensional images by the image acquirer according to a sequence defined beforehand, a slice position adjuster configured to determine a slice position from the recommended slice position calculated by the recommended slice position calculator, and a main scan controller configured to perform a main scan to acquire an image for diagnosis of the slice position determined by the slice position adjuster, and wherein:

the anatomical feature extractor is further configured to extract information on a third anatomical feature from the image for diagnosis according to the recommended slice position calculation information, the slice plane determiner is further configured to determine a fifth slice plane using either one of the information on the first anatomical feature and the information on the second anatomical feature, and the information on the third anatomical feature according to the recommended slice position calculation information, and the recommended slice position calculator is further configured to determine the fifth slice plane as a second recommended slice position.

9. The medical imaging apparatus according to claim 1, wherein:

the recommended slice position calculation storer is further configured to store types of image processing used for extracting information on the anatomical features, and the anatomical feature extractor is configured to extract the information on the anatomical features by an image processing stored in the recommended slice position calculation storer.

10. The medical imaging apparatus according to claim 1, which further comprises:

a displayer configured to display the recommended slice position calculated by the recommended slice position calculator, on a display, an input receiver configured to receive input of an adjusted value for changing the recommended slice position displayed by the displayer, and a slice position adjuster configured to adjust the recommended slice position with the received adjusted value, and determine the adjusted slice position as a slice position, when an adjusted value is received through the input receiver.

11. The medical imaging apparatus according to claim 10, which further comprises:

a learning data storer configured to store an adjusted value received through the input receiver as a correction amount corresponding to an imaging region, and wherein:

when the adjusted value corresponding to an imaging region to be imaged is stored by the learning data storing storer, the recommended slice position calculator is further configured to correct the calculated recommended slice position with the correction amount, before it is displayed by the displayer.

12. The medical imaging apparatus according to claim 1, which further comprises:

a scout scan controller configured to control acquisition of the two-dimensional images by the image acquirer according to a sequence defined beforehand, and wherein:

the scout scan controller is further configured to control to acquire the second image group after acquisition of the first image group, and the anatomical feature extractor is further configured to complete the extraction of the information on the first anatomical feature before acquisition of the second image group.

13. The medical imaging apparatus according to claim 12, which further comprises:

a scout scan information storer configured to store information for specifying the first slice plane and the second slice plane as information corresponding to an imaging region, and wherein:

the scout scan controller is further configured to control the image acquirer according to the information stored in the scout scan information storer as that for the imaging region.

14. The medical imaging apparatus according to claim 12, which further comprises:

a validity judger configured to judge validity of the slice position determined by the slice position adjuster, and a re-scout scan director configured, when the validity is denied by the validity judger, to determine a slice plane for which two-dimensional images are obtained by the image acquirer on the basis of the recommended slice position, and making the image acquirer acquire an image of that slice plane.

15. The medical imaging apparatus according to claim 1, which further comprises:

a scout scan controller configured to control acquisition of the two-dimensional images by the image acquirer according to a sequence defined beforehand, and wherein:

the scout scan controller is further configured to control to acquire the second image group after acquisition of the first image group, the anatomical feature extractor is further configured to complete the extraction of the information on the first anatomical feature before start of a sequence for acquiring the second image group, and the scout scan controller is further configured to adjust a position at which the second image group is obtained on the basis of the information on the first anatomical feature.

* * * * *